United States Patent
Balzarini et al.

(10) Patent No.: US 7,115,592 B2
(45) Date of Patent: Oct. 3, 2006

(54) PHOSPHONATE SUBSTITUTED PYRIMIDINE COMPOUNDS AND METHODS FOR THERAPY

(75) Inventors: Jan M. R. Balzarini, Heverlee (BE); Erik D. A. De Clercq, Lovenjoel (BE); Antonin Holy, Horni Pocernice (CZ); Dana Hockova, Smichov (CZ)

(73) Assignees: Institute of Organic Chemistry, (CZ); Biochemistry of the Academy of Sciences of the Czech Republic, (BE)

( * ) Notice: Subject to any disclaimer, the term of this patent is extended or adjusted under 35 U.S.C. 154(b) by 0 days.

(21) Appl. No.: 10/869,005

(22) Filed: Jun. 16, 2004

(65) Prior Publication Data

US 2005/0075318 A1    Apr. 7, 2005

Related U.S. Application Data

(60) Provisional application No. 60/478,893, filed on Jun. 16, 2003.

(51) Int. Cl.
C07F 9/6512 (2006.01)
A61K 31/505 (2006.01)

(52) U.S. Cl. .................. 514/86; 514/88; 544/243
(58) Field of Classification Search ............. 544/243; 514/86, 88
See application file for complete search history.

(56) References Cited

U.S. PATENT DOCUMENTS

| | | | |
|---|---|---|---|
| 4,659,825 A | 4/1987 | Holy et al. | |
| 4,724,233 A | 2/1988 | De Clercq et al. | |
| 4,740,365 A | 4/1988 | Yukimatsu et al. | |
| 4,808,716 A | 2/1989 | Holy et al. | |
| 5,098,443 A | 3/1992 | Parel et al. | |
| 5,141,752 A | 8/1992 | Ayer et al. | |
| 5,142,051 A | 8/1992 | Holy et al. | |
| 5,208,221 A | 5/1993 | Kim et al. | |
| 5,302,585 A | 4/1994 | Yu et al. | |
| 5,352,786 A | 10/1994 | Jindrich et al. | |
| 5,356,886 A | 10/1994 | Harnden et al. | |
| 5,952,375 A | 9/1999 | Bischofberger et al. | |
| 6,818,633 B1 * | 11/2004 | Balzarini et al. | 514/86 |

FOREIGN PATENT DOCUMENTS

| | | |
|---|---|---|
| EP | 0 269 947 A1 | 6/1988 |
| EP | 0 369 409 B1 | 5/1990 |
| EP | 0 398 231 A2 | 11/1990 |
| EP | 0 434 450 A2 | 6/1991 |
| EP | 0 454 427 A1 | 10/1991 |
| EP | 0 468 119 A1 | 1/1992 |
| EP | 0 481 214 A1 | 4/1992 |
| EP | 0 618 214 A1 | 10/1994 |
| EP | 0 630 381 B1 | 12/1994 |
| WO | WO 92/14450 | 9/1992 |
| WO | WO 94/03467 | 2/1994 |
| WO | WO 95/07920 | 3/1995 |
| WO | WO 96/33200 | 10/1996 |
| WO | WO 98/04569 | 2/1998 |
| WO | WO 03/002580 | * 1/2003 |

OTHER PUBLICATIONS

Goff, PubMed Abstract (J Gene Med 3(6):517-28), Nov.-Dec. 2001.*
Bosseray et al., PubMed Abstract (Pathol Biol (Paris) 50(8):483-92), Oct. 2002.*
Razonable et al., PubMed Abstract (Herpes 10(3):60-5), Dec. 2003.*
Douglas, Jr. Introduction to Viral Diseases, Cecil Textbook of Medicine, 20th Edition, vol. 2, pp. 1739-47, 1996.*
Balzarini et al, "Differential Antiherpesvirus and Antiretrovirus Effects of the (S) and (R) Enantiomers of Acyclic Nucleoside Phosphonates: Potent and Selective In Vitro and In Vivo Antiretrovirus Activities of (R)-9-(2- Phosphonomethoxypropyl)-2,6-Diaminopurine", 37(2):332-338, AIDS, 1993.
Balzarini et al., "9-(2-phosphonylmethoxyethyl)adenine (PMEA) effectively inhibits retrovirus replication in vitro and simian immunodeficiency virus infection in rhesus monkeys", 5:21-28, AIDS, 1991.
Cihlar et al., "Transport of 9-(2-Phosphonomethoxyethyl)Adenine across Plasma Membrane of HeLa S3 Cells Is Protein Mediated", 39(1):117-124, Antimicro AG & Chemo, 1995.
De Clercq et al, "Moloney Sarcoma Virus-Induced Tumors in Mice: Inhibition or Stiumation . . . ", 137:590-594, Proc Soc Exp Biol Med, 1971.
Egberink et al, "Suppression of feline immunodeficiency virus infection in vivo by 9-(2-phosphonomethoxyethyl)adenine", 87:3087-3091, Proc Natl Acad Sci, 1990.

(Continued)

Primary Examiner—Deepak Rao
(74) Attorney, Agent, or Firm—Mark L. Bosse

(57) ABSTRACT

Novel compounds are provided having formula (I)

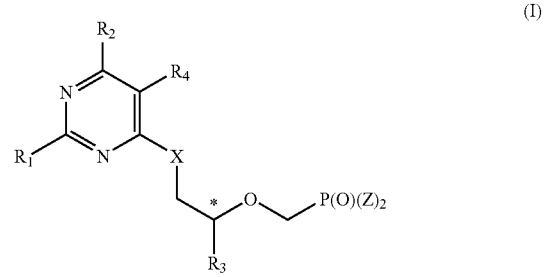

(I)

where $R_1$, $R_2$, $R_3$, $R_4$, Z, X and * are defined herein. Also provided are antiviral methods for use and processes for synthesis of the compounds of formula (I).

34 Claims, 1 Drawing Sheet

OTHER PUBLICATIONS

Eger et al., "Synthesis of New Acyclic Pyrimidine Nucleoside Analogs as Potential Antiviral Drugs", 37:3057-3061, J Med Chem, 1994.

Franchetti et al, "Acyclic Nucleotides Related To Clitocine: Synthesis and Anti-HIV Activity", 14(3-5):607-614, Nucls & Nuclt, 1995.

Greene et al, "Protection For The Hydroxyl Group, Including 1,2- and 1, 3-Diols", 2:10-142, Protective Groups in Organic Synthesis (2nd Ed.) (John Wiley & Sons), 1991.

Greene et al, "Protection For The Amino Acids", 7:309-405, Protective Groups in Organic Synthesis (2nd Ed.) (John Wiley & Sons), 1991.

Hartmann et al., "In vitro activity of acyclic nucleoside phosphonate derivatives against feline immunodeficiency virus in Crandell feline kidney cells and feline peripheral blood lymphocytes", 5(1):13-19, Antiviral Chem & Chemo, 1994.

Holy et al., "Phosphonylmethyl Ethers of Nucleosides and Their Acyclic Analogues", 401:51-71, Nucleotide Analogues, 1989.

Holy et al., "Synthesis of quaternary 1-[2-(phosphonomethoxy)ethyl]derivatives of 2,4-diaminopyrimidine and related acyclic nucleotide analogs", 64:242-256, Collect Czech Chem Commun, 1999.

Holy, A., "Structure-Activity Studies in the Series of Acyclic Nucleotide Analogues", 38(10):457-462, KEM IND, 1989.

Middleton et al, "Cyanocarbon Chemistry", 80(11):2788-2795, J Am Chem Soc, 1958.

Middleton et al, "Cyanocarbon Chemistry. IX. Heterocyclic Compounds from Dicyanoketene Acetls", 80:2829-2832, J Am Chem Soc, 1958.

Popovic et al, "Detection, Isolation, and Continuous Production of Cytopathic Retrovirus(HTLV-III)from Patients with AIDS and Pre-AIDS", 224:497-500, SCIENCE, 1984.

Thormar et al, "Inhibitory effect of 9-(2-phosphonylethoxyethyl) adenine on visna virus infection in lambs: A model for in vivo testing of candidate anti-human immunodeficiency virus drugs", 93:3283-3287, Proc Natl Acad Sci, 1995.

Van Laethem et al, "Mutations in the non-nucleoside binding-pocket interfere with the multi-nucleoside resistance phenotype", 15:553-561, AIDS, 2001.

Wormstadt et al, "Synthesis of Acyclic Nucleoside Phosphonate as Antiviral Compounds", 37:1187-1191, J Het Chem, 2000.

* cited by examiner

Table: Antiviral activity of test compounds

| Example | EC$_{50}$$^a$ (µg/ml) | | | | | | | | | CC$_{50}$$^b$ (µg/ml) |
|---|---|---|---|---|---|---|---|---|---|---|
| | HIV-1 (III$_B$) | HIV-2 (ROD) | CMV AD169 | CMV Davis | VZV OKA | VZV 07/1 | HSV-1 (KOS) | HSV-2 (G) | VV | MSV | (CEM) |
| 1 | >100 | >100 | >50 | >50 | >50 | >50 | >400 | 240 | >400 | >40 | >100 |
| 2 | >100 | >100 | >50 | >50 | >50 | >50 | >400 | 240 | >400 | >40 | >100 |
| 3 | >100 | >100 | >50 | >50 | 42 | 32 | >400 | >400 | >400 | ≥100 | >100 |
| 4a | >100 | 30 | >50 | >50 | >50 | >50 | >400 | >400 | >400 | 13.6 | >100 |
| 4b | >100 | >100 | >40 | >50 | 5 | 11 | >400 | >400 | >400 | 15.8 | >100 |
| 5 | 0.065 | 0.065 | >50 | 200 | >50 | >50 | >400 | >400 | 240 | 0.04-0.06 | 1.3-4.1 |
| 6 | >100 | >100 | >50 | >50 | | | >400 | >400 | >400 | >40 | >100 |
| 7 | >100 | >100 | >40 | 200 | | | >400 | >400 | >400 | >40 | >100 |
| 8 | 3.3 | 1.3 | | | | | >80 | >80 | >80 | 2.75 | ≥200 |
| 9 | 1.3 | 0.8 | | | | | >80 | >80 | 240 | 6.0 | 87 |
| Reference compounds | | | | | | | | | | | |
| 5-H | 0.80 | 0.43 | >50 | >50 | 1.2 | 2.5 | 6.5 | 9.6 | 48 | 0.04 | 11 |
| 5-Cl | 0.93 | 1.3 | >40 | >200 | | | >400 | >400 | >400 | 0.85 | ≥100 |
| PMEA | 0.96 | 1.9 | 30 | 77 | 8.5 | 10 | 7 | 7 | >50 | 0.62 | 16 |
| (R)-PMPA | 0.36 | 0.43 | >50 | >50 | ≥50 | ≥50 | >50 | >50 | >50 | 1.4 | 125 |

$^a$50% Effective concentration.
$^b$50% Cytostatic concentration.

Figure 1

PHOSPHONATE SUBSTITUTED PYRIMIDINE COMPOUNDS AND METHODS FOR THERAPY

This application claims the benefit of U.S. Provisional Application 60/478,893 filed Jun. 16, 2003.

BACKGROUND OF THE INVENTION

Acyclic nucleotide analogues containing phosphonate groups are disclosed for example in U.S. Pat. Nos. 4,659,825, 4,808,716, 4,724,233, 5,142,051, 5,302,585, 5,208,221, 5,352,786, 5,356,886, in EP publication numbers 269,947, 481,214, 630,381, 369,409, 454,427, 468,119, 434,450, 618,214 and 398,231 and in WO 95/07920, WO 94/03467 and WO 96/33200. The teachings of these patents and publications include compounds in which a phosphonate group is linked to a defined purine or pyrimidine base, generally at the 1- or 9-position of the pyrimidine or purine bases, respectively, by way of a 2-(methoxy)propyl group, a 2-(methoxy)ethyl group, a 2-methoxy-3-hydroxypropyl group, or a 2-methoxy-3-fluoropropyl group, known respectively as PMP, PME, HPMP and FPMP purine or pyrimidine compounds. These compounds exhibit antiviral and cytostatic activity.

Daluge et al. (34th Interscience Conference on Antimicrobial Agents and Chemotherapy, Oct. 4–7, 1994) discloses carbovir derivatives in which the 6 position of the purine is substituted with cyclopropylamino, N-cyclopropyl-N-methylamino or N-aziridinyl.

Cihlar et al., "Antimicrobial Agents and Chemotherapy" 39(1): 117–124 (1995) disclose $N^6$-aminohexyl-PMEDAP.

Holy et al., "ACS Symp. Ser." 401:57–71 (1989) and Holy, "Kem. Ind." 38(10):457–462 (1989) describe the antiviral activity of certain $N^6$-substituted nucleotide analogues.

Additional phosphonate-substituted pyrimidine analogues are disclosed by Holy et al., "Collect. Czech. Chem. Commun." 64:242–256 (1999), Eger et al., "J. Med. Chem." 37:3057–3061 (1994), Wormstadt et al., "J. Heterocyclic Chem." 37:1187–1191 (2000), and Franchetti et al., "Nucleosides & Nucleotides" 14(3–5):607–610 (1995). The latter three publications have a phosphonate-containing side-chain linked via a 6-N substituent of 2,4-disubstituted pyrimidine.

SUMMARY OF THE INVENTION

It is an object of this invention to provide novel compounds having antiviral activity, in particular against RNA or DNA viruses such as HIV, HBV or HSV.

It is an additional object to provide compounds useful in the preparation of ion exchange resins or chiral media.

It is a further object to provide intermediates and methods for making such compounds.

These and other objects will be more fully understood by further reference to the disclosures herein.

In accordance with the invention, novel compounds are provided having formula (Iaa)

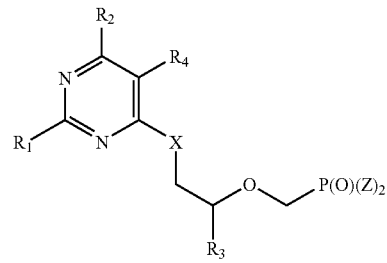

(Iaa)

wherein:
$R_1$ is H, amino, methylsulfanyl;
$R_2$ is H, methyl, halo, —$N(R_5)_2$, hydroxy, or protected hydroxy;
$R_3$ is independently H, methyl, hydroxymethyl, halomethyl, or protected hydroxymethyl;
$R_4$ is selected from:
(i) $C_1$ to $C_{10}$ alkyl,
(ii) $C_2$ to $C_{10}$ alkenyl, or,
(iii) $C_2$ to $C_{10}$ alkynyl,
(iv) $C_3$–$C_8$ cycloalkyl,
(v) aryl,
(vi) heteroaryl,
(vii) $C_7$–$C_{14}$ arylalkyl,
(viii) heteroarylalkyl,
(ix) —$CH_2OH$,
(x) —$CH_2OR_5$,
(xi) —$CH_2C(O)R_5$,
(xii) —$CH_2R_6$,
(xiii) —$CH_2OC(O)R_5$,
(xiv) —$CH_2OC(O)CH(R_7)(NHR_8)$,
(xv) —$CH_2NR_9R_{10}$,
(xvi) —$CH_2CN$,
(xvii) —$CO_2R_5$,
(xviii) —$CH_2CH_2OH$,
(xix) —$CH_2CH_2OR_5$,
(xx) —$CH_2CH_2OC(O)R_5$,
(xxi) —$CH_2CH_2OC(O)CH(R_7)(NHR_8)$,
(xxii) —$CH_2SH$,
(xxiii) —$C(O)H$,
(xxiv) —$CH_2CO_2R_9$,
(xxv) —$CH_2SO_3H$,
(xxvi) —$CH_2CH_2SO_3H$,
(xxvii) —$CH_2CH_2PO_3H_2$,
(xxviii) —$CH_2CH_2OCH_2PO_3H_2$,
(xxix) —$CH_2OPO_3H_2$,
(xxx) —$OCH_2PO_3H_2$,
(xxxi) —OH,
(xxxii) —$OR_{10}$,
(xxxiii) —$NH_2$,
(xxxiv) —$NR_{11}R_{12}$,
(xxxv) —SH,
(xxxvi) —$SR_5$,
(xxxvii) —SCN,
(xxxviii) —$N_3$,
(xxxix) —CN,
(xl) —$CONR_{11}R_{12}$,
(xli) —$CH_2CONR_{11}R_{12}$,
(xlii) —NHOH,
(xliii) —$NHOR_5$,
(xliv) —NO,
(xlv) —$NO_2$,
(xlvi) —$NHNR_{11}R_{12}$, (xlvii) 2-halovinyl,
(xlviii) 3,3,3-trifluoropropenyl,
(xlix) $C_1$–$C_{10}$ 2-(alkoxycarbonyl)ethenyl,
(l) 2-carboxyethenyl,
(li) 2-cyanoethenyl,
(lii) difluoromethyl,
(liii) trifluoromethyl,
(liv) 2,2,2-trifluoroethyl,
(lv) 2-haloethyl; and
(lvi) —$CH_2N_3$;
X independently is oxygen, sulfur, or a bond;
Z independently is hydroxy, an ester or amide;
$R_5$ is independently H, $C_1$–$C_{10}$ alkyl or a protecting group;
$R_6$ is F, Cl, Br or I;
$R_7$ is the side chain of any of the unprotected or N-protected α-amino acids;
$R_8$ is H or —$C(O)CH(R_7)(NH_2)$;
$R_9$ and $R_{10}$ are independently selected from H, $C_1$–$C_{10}$ alkyl, carboxyalkyl, aminoalkyl, and $C_2$–$C_{10}$ alkenyl, or both together form a cycle with or without participation of heteroatom;
$R_{11}$ and $R_{12}$ are independently selected from H, $C_1$ to $C_{10}$ alkyl, $C_3$–$C_8$ cycloalkyl, heteroaryl and $C_7$–$C_{12}$ arylalkyl, or both together form a cycle with or without participation of heteroatom; and
salts and solvates thereof.

In accordance with the invention, novel compounds are provided having formula (I)

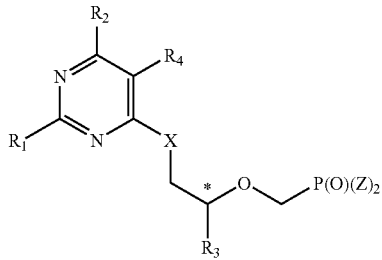

(I)

wherein * designates a chiral carbon atom; and
$R_1$ is H, amino, methylsulfanyl;
$R_2$ is H, methyl, halo, —$N(R_5)_2$, hydroxy, or protected hydroxy;
$R_3$ is independently methyl, hydroxymethyl, halomethyl, or protected hydroxymethyl;
$R_4$ is selected from:
(i) $C_1$ to $C_{10}$ alkyl,
(ii) $C_2$ to $C_{10}$ alkenyl, or,
(iii) $C_2$ to $C_{10}$ alkynyl,
(iv) $C_3$–$C_{10}$ cycloalkyl,
(v) aryl,
(vi) heteroaryl,
(vii) $C_7$–$C_{14}$ arylalkyl,
(viii) heteroarylalkyl,
(ix) —$CH_2OH$,
(x) —$CH_2OR_5$,
(xi) —$CH_2C(O)R_5$,
(xii) —$CH_2R_6$,
(xiii) —$CH_2OC(O)R_5$,
(xiv) —$CH_2OC(O)CH(R_7)(NHR_8)$,
(xv) —$CH_2NR_9R_{10}$,
(xvi) —$CH_2CN$,
(xvii) —$CO_2R_5$,
(xviii) —$CH_2CH_2OH$,
(xix) —$CH_2CH_2OR_5$,
(xx) —$CH_2CH_2OC(O)R_5$,
(xxi) —$CH_2CH_2OC(O)CH(R_7)(NHR_8)$,
(xxii) —$CH_2SH$,
(xxiii) —$C(O)H$,
(xxiv) —$CH_2CO_2R_9$,
(xxv) —$CH_2SO_3H$,
(xxvi) —$CH_2CH_2SO_3H$,
(xxvii) —$CH_2CH_2PO_3H_2$,
(xxviii) —$CH_2CH_2OCH_2PO_3H_2$,
(xxix) —$CH_2OPO_3H_2$,
(xxx) —$OCH_2PO_3H_2$,
(xxxi) —OH,
(xxxii) —$OR_{10}$,
(xxxiii) —$NH_2$,
(xxxiv) —$NR_{11}R_{12}$,
(xxxv) —SH,
(xxxvi) —$SR_5$,
(xxxvii) —SCN,
(xxxviii) —$N_3$,
(xxxix) —CN,
(xl) —$CONR_{11}R_{12}$
(xli) —$CH_2CONR_{11}R_{12}$
(xlii) —NHOH,
(xliii) —$NHOR_5$,
(xliv) —NO,
(xlv) —$NO_2$,
(xlvi) —$NHNR_{11}R_{12}$
(xlvii) 2-halovinyl,
(xlviii) 3,3,3-trifluoropropenyl,
(xlix) $C_1$–$C_{10}$ 2-(alkoxycarbonyl)ethenyl,
(l) 2-carboxyethenyl,
(li) 2-cyanoethenyl,
(lii) difluoromethyl,
(liii) trifluoromethyl,
(liv) 2,2,2-trifluoroethyl,
(lv) 2-haloethyl; and
(lvi) —$CH_2N_3$;
X independently is oxygen, sulfur, or a bond;
Z independently is hydroxy, an ester or amide;
$R_5$ is independently H, $C_1$–$C_{10}$ alkyl or a protecting group;
$R_6$ is F, Cl, Br or I;
$R_7$ is the side chain of any of the unprotected or N-protected α-amino acids;
$R_8$ is H or —$C(O)CH(R_7)(NH_2)$;
$R_9$ and $R_{10}$ are independently selected from H, $C_1$–$C_{10}$ alkyl, carboxyalkyl, aminoalkyl, and $C_2$–$C_{10}$ alkenyl, or both together form a cycle with or without participation of heteroatom;
$R_{11}$ and $R_{12}$ are independently selected from H, $C_1$ to $C_{10}$ alkyl, $C_3$–$C_8$ cycloalkyl, heteroaryl and $C_7$–$C_{12}$ arylalkyl, or both together form a cycle with or without participation of heteroatom; and
salts and solvates thereof.

Exemplary compounds of the invention include compounds of formula I and formula Iaa wherein $R_1$ and $R_2$=$NH_2$, $R_3$=H, X=O, and $R_4$=$CH_3$, CN, CH=O, $CO_2H$.

The objects also are accomplished by a method for preparation of compounds of the formula (I) and formula (Iaa)

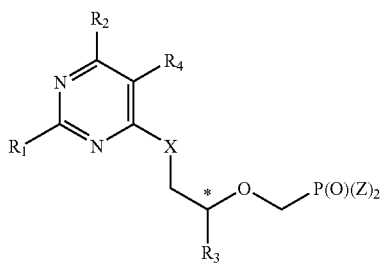

(I)

where

R$_1$, R$_2$, R$_3$, R$_4$, X, Z, R$_5$ and * are defined above; comprising reacting a compound of formula (II)

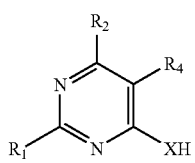

(II)

where

R$_1$ and R$_5$ are defined above;

R$_2$ is H, methyl, halo, —N(R$_5$)$_2$, hydroxy or protected hydroxy; and

X is O or S;

with a compound of the formula (III)

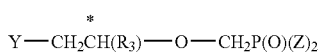

(III)

where

Z is an ester or an amide;

* designates a chiral carbon atom, when R$_3$ is not a H;

R$_3$ is H, methyl, halomethyl or protected hydroxymethyl; and

Y is a leaving group in dipolar aprotic solvent in the presence of a base to obtain a compound of formula (I) where Z is ester or amide; (b) one or both Z groups optionally are converted to produce the compound of formula (I) where at least one Z is hydroxy.

In another embodiment of this invention, a method is provided for the preparation of compounds of formula (I) and formula (Iaa) where R$_1$ is H, amino or methylsulfanyl;

R$_2$ is —N(R$_5$)$_2$

R$_3$ is independently H, methyl, hydroxymethyl, halomethyl or protected hydroxymethyl;

R$_4$ is as defined above and includes alkyl, alkenyl, alkynyl, arylalkyl, cycloalkyl, formyl (—CHO), azido (—N$_3$), amino (—NH$_2$), alkylamino (—NR$_2$), hydroxyl (—OH), alkoxy (—OR), cyano (—CN), carboxyl (—COOH), amido (—NRC(O)R, or alkoxycarbonylalkyl;

X is oxygen or sulfur;

Z independently is hydroxy, an ester or an amide;

R$_5$ is independently H, C$_1$–C$_8$ alkyl or a protecting group; and

* designates a chiral carbon atom, when R$_3$ is not a H;

comprising reacting a compound (IV) with an amine HN(R$_5$)$_2$.

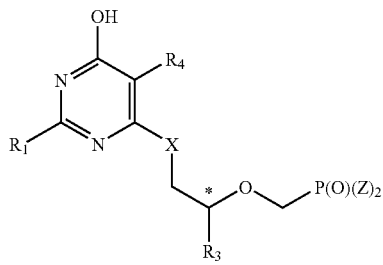

(IV)

and where compound (IV) includes substituents:

R$_3$ is H, methyl, halomethyl or protected hydroxymethyl;

X is O or S; and

Z is amide or ester.

One or both Z groups optionally are converted to the compound of formula (I) where at least one Z is hydroxy.

In another embodiment, a method is provided for preparation of compounds of formula (V)

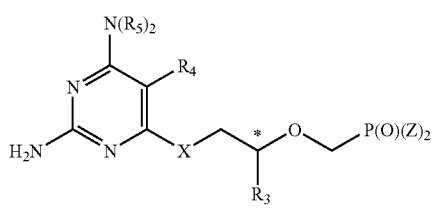

(V)

where

R$_3$ is H, methyl, hydroxymethyl, halomethyl or protected hydroxymethyl;

R$_5$ independently is H, C$_1$–C$_8$ alkyl or a protecting group;

X is oxygen or sulfur;

Z independently is hydroxy, an ester or amide; and

* designates a chiral carbon atom, when R$_3$ is not a H;

comprising reacting compound (IVa)

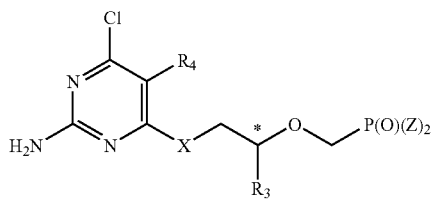

(IVa)

with N(R$_5$)$_2$ in anhydrous solvent, alkali hydroxide or alkali carbonate in aqueous solution and Z is optionally converted to the compound of formula (V) wherein 1 or 2 Z groups are hydroxy.

In another embodiment, a method is provided for the preparation of compounds of formula (VI)

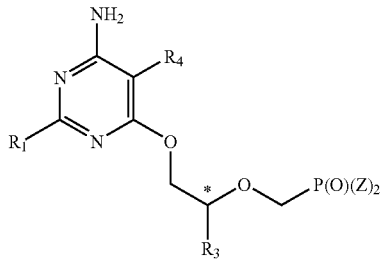

(VI)

where
R₁ is H, amino or methylsulfanyl;
R₃ is H, methyl, hydroxymethyl, halomethyl or protected hydroxymethyl;
Z independently is hydroxy, an ester or amide; and
* designates a chiral carbon atom, when R₃ is not a H; comprising reacting a compound of formula (VII)

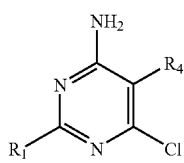

(VII)

where
R₁ is H, amino or methylsulfanyl with a compound of the formula (VIII)

(VIII)

HOCH₂CH(R₃)OCH₂P(O)(Z)₂ where Z is amide or ester in the presence of a base. Optionally one or both Z groups are converted to produce a hydroxy.

In another embodiment of this invention, a method is provided for the preparation of compounds of formula (XIII)

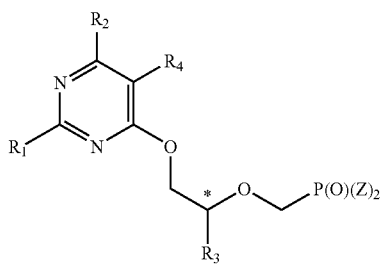

(XIII)

where
R₁ is H, amino or methylsulfanyl;
* is a chiral carbon atom, when R₃ is not a H;

R₂ is H, chloro, hydroxy or amino;
R₃ is H, methyl, halomethyl or hydroxymethyl;
R₄ is defined as above; and
Z is amide or ester;

comprising (a) reacting a compound of the formula (IX)

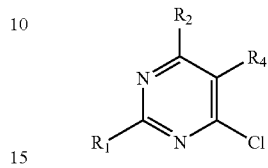

(IX)

where
R₁ is H, amino or methylsulfanyl;
R₂ is H, chloro or amino;
with a compound of the formula (X):

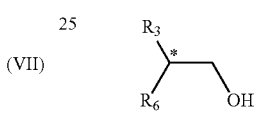

(X)

where
R₃ is H, methyl, hydroxymethyl, halomethyl or protected hydroxymethyl;
* is a chiral carbon atom, when R₃ is not a H;
R₆ is hydroxy or protected hydroxy;
or R₃ and R₆ are joined by a cyclic acetal or ketal protecting group;

in the presence of a base without solvent or in the presence of an aprotic solvent to produce a compound of formula (XI):

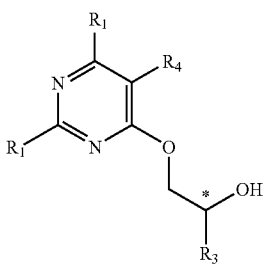

(XI)

where
R₁ is H, amino or methylsulfanyl;
* is a chiral carbon atom, when R₃ is not a H;
R₂ is H, chloro or amino; and
R₃ is H, methyl, halomethyl or protected hydroxymethyl; and (b) reacting compound (XI) with a compound of the formula (XII)

Y—CH₂P(O)(OZ)₂ (XII)

where
Y is a leaving group;
Z is amide or ester in the presence of a base in dimethylformamide or tetrahydrofuran to produce a compound of formula (XIII); and (c) optionally hydrolyzing Z group in compound (XIII)

to produce a compound of formula (VI) where 1 or 2 Z groups are hydroxy and X is oxygen atom.

In another embodiment of this invention, a method is provided for the preparation of compounds of formula (I) where
$R_1$ is H, amino or methylsulfanyl;
$R_3$ is H, methyl, hydroxymethyl, halomethyl or protected hydroxymethyl;
$R_4$ is as defined above;
X is oxygen;
Z independently is hydroxy, an ester or amide; and
* designates a chiral carbon atom, when $R_3$ is not a H;

comprising (a) reacting a compound of the formula (VI)

where
$R_1$ is H, amino or methylsulfanyl;
$R_3$ is H, methyl, hydroxymethyl, halomethyl or protected hydroxymethyl;
Z independently is an ester; and
* designates a chiral carbon atom, when $R_3$ is not a H;

with elemental halogen in an inert solvent to produce a compound of formula (I).

Optionally one or both Z groups are converted to hydroxy.

Further objects of this invention are accomplished by a method comprising administering a therapeutically effective amount of a compound of formula (I) to a patient in need of treatment for conditions including HIV, HBV, or HSV infection.

BRIEF DESCRIPTION OF THE DRAWINGS

FIG. 1 is a Table showing the antiviral activity of test compounds from Examples 1–9.

DETAILED DESCRIPTION OF THE INVENTION

The substituent variables of compounds of the present invention include the substituent variables as described in U.S. Pat. No. 5,952,375, columns 2–8, except where expressly made divergent here. The subscript and superscript descriptors are to be viewed and interpreted as interchangeable and equivalent. Following convention, certain subscripts indicate the number of substituent groups.

As used herein, and unless modified by the immediate context, "alkyl" means branched, normal or cyclic saturated hydrocarbons and includes methyl, ethyl, propyl, cyclopropyl, cyclobutyl, isopropyl, n-, sec-, iso- and tert-butyl, pentyl, isopentyl, 1-methylbutyl, 1-ethylpropyl, neopentyl, and t-pentyl.

"Substituted alkyl", "substituted aryl", and "substituted arylalkyl" mean alkyl, aryl, and arylalkyl respectively, in which one or more hydrogen atoms are each independently replaced with a substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR—S(=O)$_2$O$^-$, —S(=O)$_2$OH, —S(=O)$_2$R, —OS(=O)$_2$OR, —S(=O)$_2$ NR, —S(=O)R, —OP(=O)O$_2$RR, —P(=O)O$_2$RR—P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" as used herein includes by way of example and not limitation these heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or carboline. Still more typically, nitrogen bonded heterocycles include 1-aziridyl, 1-azetedyl, 1-pyrrolyl, 1-imidazolyl, 1-pyrazolyl, and 1-piperidinyl.

The compounds of formulae I and Ia may contain asymmetric carbon atom and thus can exist as pure enantiomers, mixtures of enantiomers or racemates. The present invention includes within its scope all of these forms. The terms "R" and "S" configuration used herein are as defined by IUPAC 1974 Recommendations for Section E, Fundamental Stereochemistry, Pure. Appl. Chem. (1976) 45, 13–30.

The term "$C_1$ to $C_{10}$ alkyl" as used herein refers to straight or branched chain alkyl radicals containing from 1 to 10 carbon atoms including, but not limited to, methyl, ethyl, isopropyl, n-butyl, isobutyl, sec-butyl, n-pentyl, 1-methylbutyl, 2,3-dimethylbutyl, 2-methylpentyl, 2,2-dimethylpropyl, n-hexyl, n-heptyl, n-octyl, n-nonyl, n-decyl and the like. The term "alkenyl" as used herein refers to $C_2$ to $C_6$ straight or branched carbon chain which contains a carbon-carbon double bond including, but not limited to, vinyl, allyl, propenyl and the like. The term "alkynyl" as used herein refers to $C_2$ to $C_6$ straight or branched carbon chain which contains a carbon-carbon triple bond including, but not limited to, ethynyl, propynyl, butynyl and the like. The term "alkoxy" as used herein refer to —$OR_{13}$ wherein $R_{13}$ is a $C_1$ to $C_{10}$ alkyl group. The term "carboxyalkyl" as used herein refers to a carboxylic acid group (—COOH) appended to a $C_1$ to $C_{10}$ alkyl radical. The term "alkoxycarbonyl" as used herein refers to —$C(O)R_{14}$ wherein $R_{14}$ is an alkoxy group. The term "aminoalkyl" as used herein refers to an amino group appended to a $C_1$ to $C_{10}$ alkyl radical. The term "halo" or "halogen" as used herein refers to Cl, Br, F or I. The term "alkylamino" as used herein refers to —$NHR_{15}$ wherein $R_{15}$ is a $C_1$ to $C_{10}$ alkyl group. The term "dialkylamino" as used herein refers to —$NR_{16}R_{17}$ wherein $R_{16}$ and $R_{17}$ are independently selected from $C_1$ to $C_{10}$ alkyl or both together form a cycle with or without participation of hetero atom. The term "side chain of any of the naturally occurring amino acids" as used herein refers to the functionality appended at the β-carbon of any of the naturally occurring amino acids and includes, but is not limited to hydrogen, methyl, isopropyl, hydroxymethyl, benzyl, and the like. The term "aralkyl $C_7$–$C_{12}$" as used herein refers to substituted arylmethyl, or 2-arylethyl group. The term "aryl" as used herein refers to phenyl or naphthyl group. The term "heteroaryl" as used herein refers to a heterocyclic group which has a similar structure and similar properties when compared to an aryl group. In addition, heteroaryl may contain different atoms and not necessarily the same number of atoms as long as it possesses the same total or valence electrons in the same arrangement as does an aryl group. Heteroaryl groups include, but are not limited to, substituents derived by hydrogen abstraction from CH or $CH_2$ groups in pyrrole, pyrrolidine, imidazole, pyridine, pyrimidine, pyridazine, quinoline, piperidine, morfoline, 1,3-dioxolane or 1,4-dioxane, and the like. "Heteroarylalkyl" as used herein refers to a heterocyclic group linked by carbon atom to $C_1$–$C_6$ alkyl. The term "N-protecting group" as used herein refers to those groups intended to protect nitrogen atoms against undesirable reactions during synthetic procedures and includes, but is not limited to, formyl, acetyl, pivaloyl, t-butylacetyl, trichloroethoxycarbonyl, t-butyloxycarbonyl (BOC), benzyloxycarbonyl (Cbz) or benzoyl groups or other nitrogen protecting groups known to those skilled in organic synthesis.

$R_3$ typically is H or methyl, but may be hydroxymethyl (typically (S) configuration substantially free (>90% S and <10% R) of the (R) enantiomer) or halomethyl. If $R_3$ is methyl or halomethyl, the carbon may be in the (2R) configuration substantially free of the (2S) configuration. Halomethyl, for example, may be fluoromethyl.

As is further described infra, Z is suitably any ester or amide heretofore known for use with nucleotide phosphonates. When Z is an ester, it has the structure $OR_7$. $R_7$ ordinarily is H (i.e., Z is hydroxy) in compounds having antiviral activity per se, although other $R_7$ ester groups described below are suitable for use as protecting groups or as pro-functionalities for prodrug embodiments.

Z is an ester or amide when it is desired to protect the compounds of this invention against undesired reactions or when the object is to provide an in vivo prodrug of the compound. Otherwise, Z is OH.

The esters or amides are useful as protected intermediates in the synthesis of compounds of this invention where Z=OH. In this embodiment, the selection of ester or amide may not be important, depending upon the nature of the reaction involved. All that is needed is that the Z substituent not be removed until the step in synthesis at which this is desired, and if this is not apparent on theoretical grounds it can be readily determined by rudimentary experiments. For example, esters in particular are used to protect the phosphonate hydroxy groups against alkylation.

When Z serves as a prodrug functionality, the ester or amide is removed in vivo from the phosphonate. Suitable prodrug esters or amidates optionally are selected based on the substrate specificity of esterases and/or carboxypeptidases expected to be found within cells where precursor hydrolysis is desired. To the extent that the specificity of these enzymes is unknown, one will screen a plurality of nucleotide analogues of this invention until the desired substrate specificity is found. This will be apparent from the appearance of free phosphonate or antiviral activity. One generally selects compounds that are (i) not hydrolyzed or hydrolyzed comparatively slowly in the upper gut, (ii) gut and cell permeable and (iii) are hydrolyzed in the cell cytoplasm and/or systemic circulation. Screens with cells from particular tissues are used to identify precursors that are released in organs susceptible to a target viral or microbial infection, e.g. in the case of liver, precursor drugs capable of hydrolysis in the liver. Other infections, e.g. CMV or HIV, optionally are treated with a precursor that is hydrolyzed at substantially the same rate and to substantially the same degree in all tissues. Assays known in the art are suitable for these purposes, including intestinal lumen stability, cell permeation, liver homogenate stability and plasma stability assays. These assays are used to determine the bioavailability characteristics of the precursors.

Typical examples of ester and amide substituents group Z are found in WO95/07920, WO98/04569 and EP 481214 A1. Any ester or amide genus or species described in these publications (and in the preference order set forth in such publications) can be used as group Z herein.

Usually, both Z are hydroxyl or both are ester and/or amide, i.e, typically 2 or no Z groups are hydroxy. In general, when neither Z is OH then one Z is amide and one is ester. Amides with naturally occurring amino acids and esters with phenyl are exemplary. The free carboxyl(s) of amino acid Z groups may be esterified with $C_1$–$C_8$ alkyl.

In general, Z is hydroxy in compounds to be used directly for antiviral purposes, i.e. such compounds are employed without any requirement for hydrolysis in vivo of the ester or amide.

Protecting groups for hydroxyl include acetals, ketals or $C_1$–$C_8$ alkyl. A typical protecting group for amino is trityl. Other conventional protecting groups are known (Greene et al., "Protecting Groups in Organic Synthesis, $2^{nd}$ Ed. 1991, pp. 10–142 and 309–405).

Utilities

The compounds of the invention are useful for the treatment of viruses, or as intermediates in the preparation of such compounds. Exemplary viral infections to be treated or to be tested for susceptibility to compounds of this invention include infections caused by DNA or RNA viruses such as herpesviruses (CMV, HSV 1, HSV 2, EBV, varicella zoster virus [VZV], bovid herpesvirus type 1, equine herpesvirus type 1, HHV-6, papillomaviruses (HPV types 1–55 including carcinogenic HPV), flaviviruses (including yellow fever virus, African swine fever virus and Japanese encephalitis virus), togaviruses (including Venezuelan equine encephalomyelitis virus), influenza viruses (types A–C), retroviruses (HIV-1, HIV-2, HTLV-I, HTLV-II, SIV, FeLV, FIV, MOMSV), adenoviruses (types 1–8), poxviruses (vaccinia virus), enteroviruses (poliovirus types 1–3, Coxsackie, hepatitis A virus, and ECHO virus), gastroenteritis viruses (Norwalk viruses, rotaviruses), hantaviruses (Hantaan virus), polyomavirus, papovaviruses, rhinoviruses, parainfluenza virus types 1–4, rabies virus, respiratory synctial virus (RSV), hepatitis viruses A, B, C and E, and the like.

Compounds of the invention include compounds effective for the treatment of herpes viruses, hepadna viruses and HIV in which $R_1$=$NH_2$, $R_2$=$NH_2$ or OH, X=O and $R_3$=H or methyl. Other antiviral activities of compounds of this invention are determined by routine assay of antiviral activity using enzyme inhibition assays, tissue culture assays, animal model assays and the like as will be understood by those skilled in the art.

The novel compounds of this invention also are useful per se or as intermediates in the preparation of polymers having a wide variety of diagnostic, therapeutic and industrial utilities.

The compounds of this invention are suitable as intermediates to prepare affinity absorption media bearing substituent groups having properties useful for absorbing compounds from impure mixtures. These are prepared and used in the same fashion as other ion exchange media containing the same substituents, e.g. phosphonate or amino. For example, the phosphonate group of the compounds herein are covalently bound to insoluble matrix and free $R_1$ amino substituents on the heterocyclic base serve as ion exchange sites. Alternatively, the heterocyclic base amino group is linked to the matrix and the free phosphonate group is then useful in the chromatographic absorption of positively charged molecules. Other immobilized embodiments of the compounds herein are useful in purifying proteins, e.g., enzymes to which the compounds of this invention may bind, e.g. transport proteins (see Cihlar, supra).

Suitable methods of incorporation of the compounds of this invention into insoluble matrices such as polymeric resins will be readily apparent to the skilled artisan. The compounds herein can be immobilized by covalently crosslinking the pyrimidine amino or hydroxy groups to an insoluble matrix. Similarly, compounds of this invention are incorporated into insoluble resins by binding the hydroxy of the phosphonate group or a hydroxymethyl $R_3$ group to the matrix or resin using covalent linking agents heretofore known. Suitable linking methods are described in Cihlar (supra).

The compounds of this invention also are useful as cross-linkers or spacers in preparing affinity absorption matrices (as opposed to functioning as affinity moieties per se as noted in the preceding paragraphs). The compounds herein contain a multiplicity of functional groups that are suitable as sites for cross-linking desired substances. It is conventional to link affinity reagents such as hormones, peptides, antibodies, enzymes, drugs, and the like to insoluble substrates. These insolubilized reagents are employed in known fashion to absorb substances from manufactured preparations, diagnostic samples and other impure mixtures. Similarly, immobilized enzymes are used to perform catalytic conversions with facile separation of enzyme from product.

In some embodiments, it is not necessary that the compounds of this invention be cross-linked to insoluble materials. For example, they can be used to link analytes to detectable groups in preparing soluble diagnostic reagents.

Methods for cross-linking using the substituent groups found in the compounds of this invention are well known in the art. For example, the phosphonic acid is used to form esters with alcohols or amides with amines. Similarly, the amino, halo, hydroxy and other reactive sites found on the pyrimidine are suitable. Of course, protection of reactive groups will be used where necessary while assembling the cross-linked reagent. In general, the inventive compounds are used by linking them through phosphonic acid to the hydroxy or amino groups of the linking partner, and covalently bonded to the other binding partner through another substituent of the compound of this invention. For example a first binding partner such as a steroid hormone is esterified to the phosphonic acid of this invention and then this conjugate is cross-linked through $R_3$ hydroxymethyl to cyanogen bromide activated Sepharose, whereby the immobilized steroid is obtained. Other chemistries for conjugation are well known. See, for example Maggio, "Enzyme-Immunoassay" (CRC, 1988, pp 71–135) and references cited therein.

Pharmaceutical Formulations

The compounds of this invention and their physiologically acceptable salts and solvates (hereafter collectively referred to as the active ingredients) are formulated for administration by any route appropriate to the condition to be treated. The compounds and formulations preferably will be sterile.

The active ingredients are placed into pharmaceutical formulations. The formulations, both for veterinary and for human use, comprise at least one active ingredient, as above defined, together with one or more acceptable carriers therefor and optionally other therapeutic ingredients. The carrier (s) must be "acceptable" in the sense of being compatible with the other ingredients of the formulation and not deleterious to the recipient.

The formulations conveniently are presented in unit dosage form and may be prepared by any of the methods well known in the art of pharmacy. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

For external infections of the eye or other external tissues e.g. mouth and skin, the formulations may be applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), typically 0.2 to 15% w/w and most typically 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxy groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogues.

The oily phase of the emulsions of this invention may be constituted from known ingredients in a known manner. This phase may comprise an emulsifier alone, or a mixture of at least one emulsifier with a fat or an oil or with both a fat and an oil. An hydrophilic emulsifier may be included together with a lipophilic emulsifier to act as a stabilizer. Emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate. Suitable oils or fats include straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate or 2-ethylhexyl palmitate. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is typically is present in such formulations in a concentration of 0.01 to 20% by weight.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered by rapid inhalation through the nasal passage from a container of the powder. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Unit dosage formulations may contain a daily dose or unit daily sub-dose, as herein above recited, or an appropriate fraction thereof, of an active ingredient.

The present invention further provides veterinary compositions comprising at least one active ingredient as above defined together with a veterinary carrier therefor. Veterinary carriers are materials for administering the composition and may be solid, liquid or gaseous materials which are otherwise inert or acceptable in the veterinary art and are compatible with the active ingredient. These veterinary compositions may be administered orally, parenterally or by any other desired route.

Compounds herein optionally are used in controlled release pharmaceutical formulations containing as active ingredient one or more active compounds in which the release of the active ingredient is controlled and regulated to allow less frequent dosing or to improve the pharmacokinetic or toxicity profile of a given compound. In general, the compounds are administered from controlled release systems such as the implant of WO 92/14450 or U.S. Pat. No. 5,098,443, or the matrices of U.S. Pat. No. 4,740,365 or U.S. Pat. No. 5,141,752. Many others are known and are suitable for use herein.

Therapeutic Administration

Suitable routes for administration include oral, rectal, nasal, topical (including ocular, buccal and sublingual), vaginal and parenteral (including subcutaneous, intramuscular, intravitreous, intravenous, intradermal, intrathecal and epidural). A preferred route of administration will depend upon the condition of the patient, the toxicity of the compound and the site of infection, among other considerations known to the clinician.

For each of the above-indicated therapeutic indications the amount required of an active ingredient (as above defined) will depend upon a number of factors including the severity of the condition to be treated, the infectious agent, whether the use is prophylactic or to treat an acute infection, the site of infection or pathology and other factors ultimately at the discretion of the attending physician or veterinarian. In general, however, a suitable dose for consideration by the clinician will be in the range of analogous methoxyphosphonates (see supra), taking into account differences in potency in in vitro testing, generally 0.1 to 250 mg per kilogram bodyweight of recipient per dose (including active ingredient(s) in a range between 0.1 mg and 400 mg/Kg/dose in increments of 0.5 mg/Kg/dose such as 2.5 mg/Kg/dose, 3.0 mg/Kg/dose, 3.5 mg/Kg/dose, etc), typically in the range 0.5 to 50 mg per kilogram body weight per dose and most usually in the range 1 to 300 mg per kilogram body weight per dose.

The desired dose is administered at appropriate intervals in unit dosage forms, usually with a relatively higher induction dose and lower, less frequent maintenance doses. The compounds also are used prophylactically, for example, by administration on about from 1 to 7 days before viral infection. HPV tumors or growths and herpes lesions often are treated topically, either by local injection or by topical gels, ointments or the like.

The compounds of the invention optionally are employed in combination with other therapeutic agents for the treatment or prophylaxis of the infections or conditions indicated above. Examples of such further therapeutic agents include agents that are effective for the treatment or prophylaxis of viral infections. These include but are not limited to the NRTIs, 3'-azido-3'-deoxythymidine (zidovudine, AZT), 2'-deoxy-3'-thiacytidine (3TC), 2',3'-dideoxy-2',3'-didehydrothymidine (D4T), carbovir (carbocyclic 2',3'-dideoxy-2',3'-didehydroguanosine), abacavir (ABC), 2',3'-dideoxyinosine (ddI), didanosine, 2′,3′-dideoxycytidine (ddc, zalcitabine), 3′-azido-2′,3′-dideoxyuridine, (E)-5-(2-bromovinyl)-2′-deoxyuridine (BVDU), 2-chloro-2′-deoxyadenosine, 2-deoxycoformycin, 5-fluorouracil, 5-fluorouridine, 5-fluoro-2′-deoxyuridine, 5-trifluoromethyl-2′-deoxyuridine, 6-azauridine, 5-fluoroorotic acid, methotrexate, triacetyluridine, 1-(2′-deoxy-2′-fluoro-1-β-D-arabinosyl)-5-iodocytidine (FIAC), tetrahydroimidazo(4,5,1-jk)-(1,4)-benzodiazepin-2(1H)-thione (TIBO) or other non-nucleoside reverse transcriptase inhibitors (e.g. nevirapine, delaviridine, efavirens, daparivine, etc.), protease inhibitors (e.g. saquinavir, indinavir, ritonovir, amprenavir, and the like), 2′-nor-cyclicGMP, 6-methoxypurine arabinoside (ara-M), 6-methoxypurine arabinoside 2′-O-valerate, cytosine arabinoside (ara-C), acyclic nucleosides such as acyclovir, valacyclovir, penciclovir, famciclovir, ganciclovir, acyclic nucleotide analogues such as HPMPC, PMEA, PMEG, PMPA, PMPDAP, FPMPA, HPMPA and HPMPDAP, (2R, 5R)-9-[tetrahydro-5-(phosphonomethoxy)-2-furanyl]adenine, (2R, 5R)-1-[tetrahydro-5-(phosphonomethoxy)-2-furanyl]thymine, other antivirals including ribavirin (adenine arabinoside), 2-thio-6-azauridine, tubercidin, aurintricarboxylic acid, 3-deazaneoplanocin, neoplanocin, rimantidine, adamantine, and foscanet (trisodium phosphonoformate.

Synthesis Methods

Compounds falling within the formula (I) are synthesized by alkylating the corresponding 6-hydroxypyrimidine base with dialkyl 2-chloroethoxymethylphosphonate (or its analogues yielding other $R_3$ groups) in the presence of NaH, $Cs_2CO_3$ or DBU (1,8-diazabicyclo[5.4.0]undec-7-ene) in dipolar aprotic solvent, usually DMF, optionally followed by deprotection, e.g. with bromotrimethylsilane and subsequent hydrolysis. The product of the formula (I) is accompanied by formation of varying amounts of the corresponding N1-isomer, i.e. 2,4-disubstituted 1-[2-(phosphonomethoxy)ethyl] pyrimidin-6-one. It can be removed by chromatography as the neutral diester prior to the bromotrimethylsilane treatment.

Another method of preparation of compounds of the formula (I) comprises the transformation of 2-substituted 4-chloro-6-[2-(phosphonomethoxy)ethoxy]pyrimidine derivatives (and its $R_3$ analogues) by reaction with primary or secondary amines in anhydrous solvents (e.g. ethanol), alkali hydroxide or alkali carbonate in water. This reaction can be catalyzed e.g. by 1,3,5-triazole, imidazole, or, to an advantage, with DABCO (diazabicyclooctane). The protecting groups optionally are then removed, e.g. by bromotrimethylsilane treatment and hydrolysis.

Compounds of formula (I) can be also obtained by the reaction of 2,4-disubstituted 6-halogenopyrimidines with sodium alkoxide of dialkyl 2-hydroxyethylphosphonate (or its analogues yielding other $R_3$ groups) followed by optional deprotection. The advantage of this procedure consists in the formation of the required O6-isomer only. The selection of the suitable synthetic procedure depends on the availability of the heterocyclic pyrimidine derivative used as a starting material.

Compounds of formula (I) can be also obtained by the reaction of 2,4-disubstituted 6-(2-hydroxyalkyl)pyrimidines with dialkyl p-toluenesulfonyloxymethylphosphonate or dialkyl bromomethylphosphonate in the presence of NaH. The starting materials are prepared by treatment of the appropriate 6-chloropyrimidine with a protected or unprotected diol in the presence of a base.

Compounds of formula (I) can be further obtained by substitution at diverse positions of the pyrimidine ring.

Z group amides or esters are converted to hydroxyl by hydrolysis.

Monoesters are easily available from the diester or a mixture of di- and monoesters by treatment with lithium or sodium azide in DMF (A. Holy, "Synthesis 1998" 381–385 (1998)).

All citations are expressly incorporated by reference.

The invention will be more fully understood by reference to the following Examples.

EXAMPLE 1

5-Allyl-2,4-diamino-6-[2-(phosphonomethoxy) ethoxy]pyrimidine

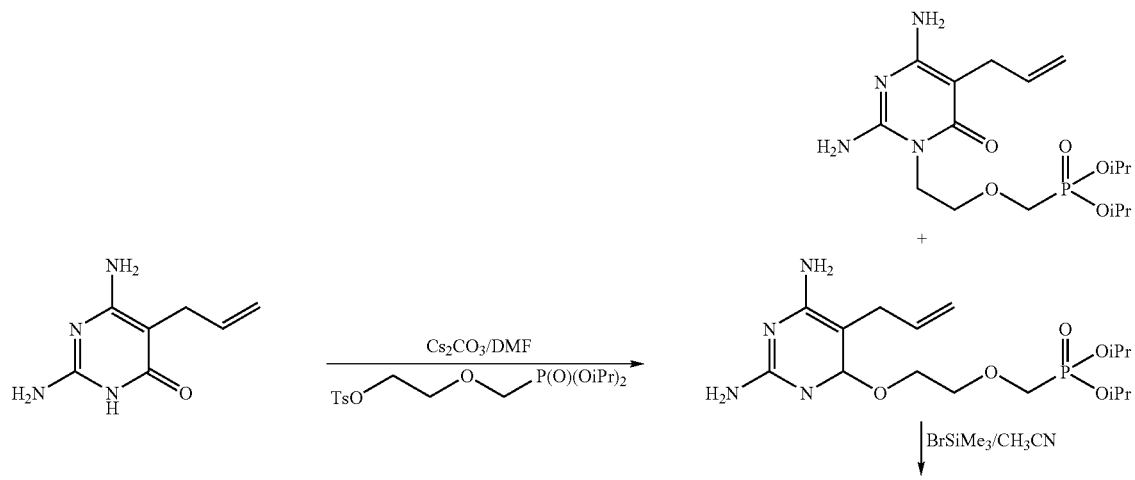

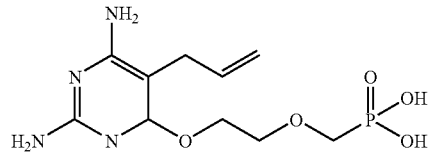

5-Allyl-2,4-diamino-6-hydroxypyrimidine (0.66 g, 4 mmol) was codistilled with toluene and the residue was sonicated with dimethylformamide (7 ml) and cesium carbonate (0.65 g, 2 mmol) and heated to 80° C. 2-[(Diisopropoxyphosphoryl)methoxy]ethyl tosylate (1.7 g, 4.4 mmol, 1.1 eq.) was added, the reaction mixture was heated at 100° C. for 20 h, evaporated in vacuo and codistilled with toluene and ethanol. The residue was treated with hot chloroform, filtered and the filtrate taken down in vacuo. Preparative HPLC afforded N1- and O6-isomers as colorless foams (0.25 g, 16% of each).

O6-Isomer (5-allyl-2,4-diamino-6-[2-(diisopropylphosphorylmethoxy) ethoxy]pyrimidine, 0.2 g, 0.5 mmol), acetonitrile (10 ml) and BrSiMe$_3$ (1 ml) was stirred overnight at room temperature. After evaporation in vacuo and codistillation with acetonitrile, the residue was treated with water and conc. aqueous ammonia was added to alkaline reaction. The mixture was evaporated to dryness and the residue was applied onto column of Dowex 50×8 (H$^+$-form, 20 ml) and washed with water. Elution with 2.5% aqueous ammonia and evaporation in vacuo afforded crude product as ammonium salt. This residue in minimum volume of water was applied on Dowex 1×2 (acetate, 25 ml) column, which was then washed with water followed by gradient of acetic acid (0–1 M). The main UV absorbing fraction was evaporated, the residue was 3-times codistilled with water and crystallized from water—ethanol to afford product as a white solid: (113 mg, 75%), mp 240–241° C. For C$_{10}$H$_{17}$N$_4$O$_5$P (304.2) calculated 39.48% C, 5.63% H, 18.42% N, 10.18% P; found 39.16% C, 5.69% H, 18.19% N, 10.17% P. FAB$^-$MS: 303 (M−H$^-$) (25). $^1$H NMR (DMSO-d$_6$): 5.98 brs, 2H, and 5.92 brs, 2H(NH$_2$); 5.73 ddt, 1H, J(2",1")=6.1, J(2",3") 10.0 and 17.1, (H-2"); 5.00 brd, 1H, J(3$_t$",2")=17.1 (H-3"$_{trans}$); 4.88 brd, 1H, J(3$_c$",2")=10.0 (H-3"$_{cis}$); 4.27 m, 2H(H-1'); 3.73 m, 2H, (H-2'); 3.57 d, 2H, J(P,CH)=8.3 (P—CH$_2$); 3.00 brd, 2H, J(1",2")=6.1 (H-1").

EXAMPLE 2

5-Benzyl-2,4-diamino-6-[2-(phosphonomethoxy)ethoxy]pyrimidine

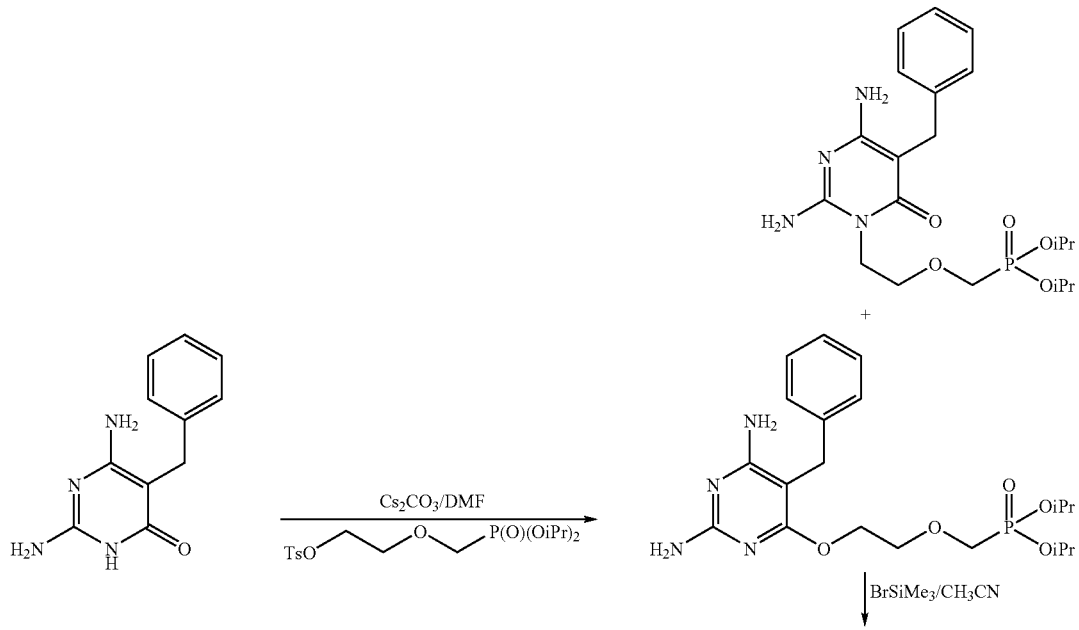

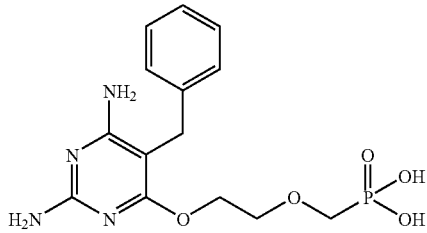

5-Benzyl-2,4-diamino-6-hydroxypyrimidine (0.86 g, 4 mmol) was codistilled with toluene and the residue was sonicated with dimethylformamide (7 ml) and cesium carbonate (0.65 g, 2 mmol) and heated to 80° C. 2-[(Diisopropoxyphosphoryl)methoxy]ethyl tosylate (1.7 g, 4.4 mmol, 1.1 eq.) was added, the reaction mixture was heated at 110° C. for 26 h, evaporated in vacuo and codistilled with toluene and ethanol. The residue was treated with hot chloroform, filtered and the filtrate taken down in vacuo. Preparative HPLC afforded N1-isomer (0.25 g, 14%) and 06-isomer (0.40 g, 32%).

O6-Isomer (5-benzyl-2,4-diamino-6-[2-(diisopropylphosphorylmethoxy) ethoxy]pyrimidine, 0.22 g, 0.5 mmol), acetonitrile (10 ml) and $BrSiMe_3$ (1 ml) was stirred overnight at room temperature. After evaporation in vacuo and codistillation with acetonitrile, the residue was treated with water and conc. aqueous ammonia was added to alkaline reaction. The mixture was evaporated to dryness and the residue was applied onto column of Dowex 50×8 ($H^+$-form, 20 ml) and washed with water. Elution with 2.5% aqueous ammonia and evaporation in vacuo afforded crude product as ammonium salt. This residue in minimum volume of water was applied on Dowex 1×2 (acetate, 25 ml) column, which was then washed with water followed by gradient of acetic acid (0–1 M). The main UV absorbing fraction was evaporated, the residue was 3-times codistilled with water and crystallized from water-ethanol to afford product as a white solid: (121 mg, 68%), mp 241–242° C. For $C_{14}H_{19}N_4O_5P \cdot 2/3H_2O$ (366.3) calculated 45.31% C, 5.66% H, 15.46% N; found 45.64% C, 5.38% H, 15.28% N. FABMS: 355 ($MH^+$) (50). $^1H$ NMR (DMSO-$d_6$): 7.23 m, 4H and 7.10 m, 1H (arom-H); 6.15 brs, 4H($NH_2$); 4.30 m, 2H(H-1'); 3.74 m, 2H(H-2'); 3.62 s, 2H(H-1"); 3.58 d, 2H, J(P,CH)=8.6 (P—$CH_2$). $^{13}C$ NMR ($D_2O$): 168.05 (C-6); 163.70 (C-4); 160.70 (C-2); 139.95, 128.74, 2 C, 127.89, 2 C, and 126.32 (arom-C); 90.38 (C-5); 70.66 d, J(P,C)=8.8 (C-2'); 67.75 d, J(P,C)=149.4 (P—C); 65.66 (C-1'); 27.50 (C-1").

EXAMPLE 3

5-Cyanomethyl-2,4-diamino-6-[2-(phosphonomethoxy)ethoxy]pyrimidine

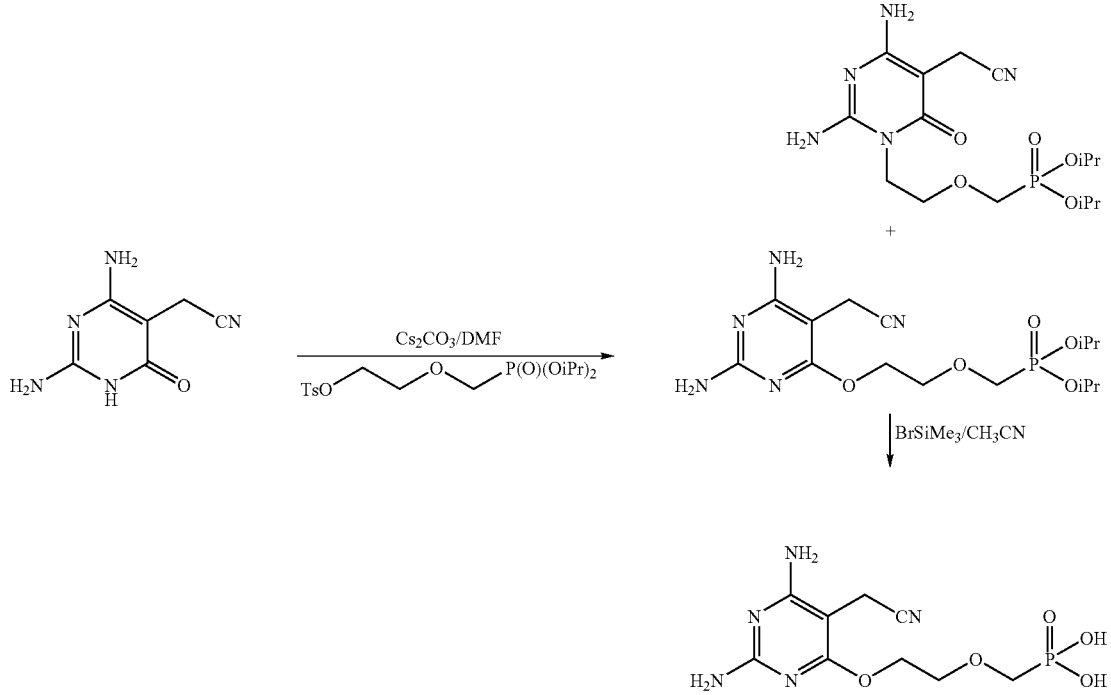

5-Cyanomethyl-2,4-diamino-6-hydroxypyrimidine (0.66 g, 4 mmol) was codistilled with toluene and the residue was sonicated with dimethylformamide (7 ml) and cesium carbonate (0.65 g, 2 mmol) and heated to 80° C. 2-[(Diisopropoxyphosphoryl) methoxy]ethyl tosylate (1.7 g, 4.4 mmol, 1.1 eq.) was added, the reaction mixture was heated at 110° C. for 10 h, evaporated in vacuo and codistilled with toluene and ethanol. The residue was treated with hot chloroform, filtered and the filtrate taken down in vacuo. Preparative HPLC afforded N1-isomer (0.25 g, 16%) and O6-isomer (0.26 g, 17%).

O6-Isomer (5-cyanomethyl-2,4-diamino-6-[2-(diisopropylphosphorylmethoxy) ethoxy]pyrimidine, 0.19 g, 0.5 mmol), acetonitrile (10 ml) and BrSiMe$_3$ (1 ml) was stirred overnight at room temperature. After evaporation in vacuo and codistillation with acetonitrile, the residue was treated with water and conc. aqueous ammonia was added to alkaline reaction. The mixture was evaporated to dryness and the residue was applied onto column of Dowex 50×8 (H$^+$-form, 20 ml) and washed with water. Elution with 2.5% aqueous ammonia and evaporation in vacuo afforded crude product as ammonium salt. This residue in minimum volume of water was applied on Dowex 1×2 (acetate, 25 ml) column, which was then washed with water followed by gradient of acetic acid (0–1 M). The main UV absorbing fraction was evaporated, the residue was 3-times codistilled with water and crystallized from water—ethanol to afford product as a white solid: (123 mg, 81%), mp 258–259° C., decomp. For C$_9$H$_{14}$N$_5$O$_5$P (303.2) calculated 35.65%; C, 4.65%; H, 23.10%; N, 10.22%; P, found 35.21%; C, 4.70%; H, 22.65%; N, 10.11%; P. FABMS: 304 (MH$^+$) (60). $^1$H NMR (DMSO-d$_6$): 6.28 brs, 2H, and 6.02 brs, 2H(NH$_2$); 4.31 m, 2H(H-1'); 3.75 m, 2H(H-2'); 3.53 d, 2H, J(P,CH)=8.2 (P—CH$_2$); 3.49 s, 2H(H-1").

EXAMPLE 4

5-Ethoxycarbonylmethyl-2,4-diamino-6-[2-(phosphonomethoxy)ethoxy]pyrimidine and 5-Carboxymethyl-2,4-diamino-6-[2-(phosphonomethoxy)ethoxy]pyrimidin 5-Ethoxycarbonylmethyl-2,4-diamino-6-hydroxypyrimidine (1.70 g, 8 mmol) was codistilled with toluene and the residue was sonicated with dimethylformamide (15 ml) and cesium carbonate (1.3 g, 4 mmol) and heated to 80° C. 2-[(Diisopropoxyphosphoryl) methoxy]ethyl tosylate (3.4 g, 8.8 mmol, 1.1 eq.) was added, the reaction mixture was heated at 100° C. for 20 h, evaporated in vacuo and codistilled with toluene and ethanol. The residue was treated with hot chloroform, filtered and the filtrate taken down in vacuo. Preparative HPLC afforded N1-isomer (050 g, 15%) and O6-isomer (0.44 g, 13%).

O6-Isomer (5-ethoxycarbonylmethyl-2,4-diamino-6-[2-(diisopropylphosphorylmethoxy)ethoxy]pyrimidine, 0.38 g, 1 mmol), acetonitrile (20 ml) and BrSiMe$_3$ (2 ml) was stirred overnight at room temperature. After evaporation in vacuo and codistillation with acetonitrile, the residue was treated with water and conc. aqueous ammonia was added to alkaline reaction. The mixture was evaporated to dryness and the residue was applied onto column of Dowex 50×8 (H$^+$-form, 40 ml) and washed with water. Elution with 2.5% aqueous ammonia and evaporation in vacuo afforded crude product as ammonium salt. This residue in minimum volume of water was applied on Dowex 1×2 (acetate, 40 ml) column, which was then washed with water followed by gradient of acetic acid (0–1 M). The two main UV absorbing fractions were evaporated, the residues were 3-times codistilled with water and crystallized from water—ethanol to afford both products as a white solids:

5-Ethoxycarbonylmethyl-2,4-diamino-6-[2-(phosphonomethoxy)ethoxy]pyrimidine: eluted by 0.25 M AcOH, (130 mg, 34%), mp 199–200° C. For C$_{11}$H$_{19}$N$_4$O$_7$P·2H$_2$O (386.3) calculated 34.20%; C, 6.00%; H, 14.50%; N, found 34.30%; C, 5.83%; H, 14.57%; N.

FABMS: 351 (MH$^+$) (20). $^1$H NMR (DMSO-d$_6$): 6.21 brs, 2H and 6.12 brs, 2H(NH$_2$); 4.24 m, 2H(H-1'); 4.04 q, 2H, J(CH$_2$,CH$_3$)=7.1 (O—CH$_2$); 3.70 m, 2H(H-2'); 3.54 d, 2H, J(P,CH)=8.5 (P—CH$_2$); 3.30 s, 2H(H-1"); 1.17 t, 3H, J(CH$_3$, CH$_2$)=7.1 (CH$_3$).

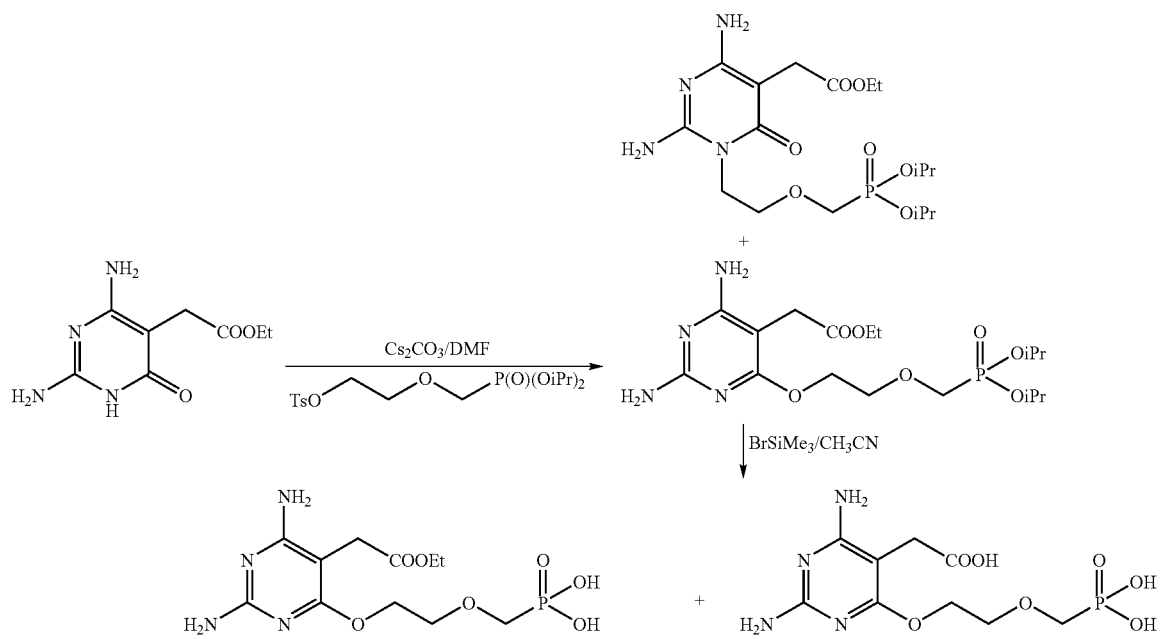

5-Carboxymethyl-2,4-diamino-6-[2-(phosphonomethoxy)ethoxy]pyrimidine: eluted by 0.5–1.0 M AcOH, (72 mg, 22%), mp 228–229° C. For $C_9H_{15}N_4O_7P \cdot H_2O$ (341.2) calculated 31.77%; C, 5.04%; H, 16.47%; N, found 31.88%; C, 4.87%; H, 16.34%; N.

FABMS: 323 (MH$^+$) (20). $^1$H NMR (DMSO-$d_6$): 6.21 brs, 2H and 6.14 brs, 2H(NH$_2$); 4.26 m, 2H(H-1'); 3.70 m, 2H(H-2'); 3.55 d, 2H, J(P,CH)=8.5 (P—CH$_2$); 3.21 s, 2H (H-1").

EXAMPLE 5

5-Methyl-2,4-diamino-6-[2-(phosphonomethoxy)ethoxy]pyrimidine

O6-Isomer (5-methyl-2,4-diamino-6-[2-(diisopropylphosphorylmethoxy)ethoxy]pyrimidine, 0.18 g, 0.5 mmol), acetonitrile (10 ml) and BrSiMe$_3$ (1 ml) was stirred overnight at room temperature. After evaporation in vacuo and codistillation with acetonitrile, the residue was treated with water and conc. aqueous ammonia was added to alkaline reaction. The mixture was evaporated to dryness and the residue was applied onto column of Dowex 50×8 (H$^+$-form, 20 ml) and washed with water. Elution with 2.5% aqueous ammonia and evaporation in vacuo afforded crude product as ammonium salt. This residue in minimum volume of water was applied on Dowex 1×2 (acetate, 25 ml) column, which was then washed with water followed by gradient of acetic acid (0–1 M). The main UV absorbing fraction was evaporated, the residue was 3-times codistilled with water

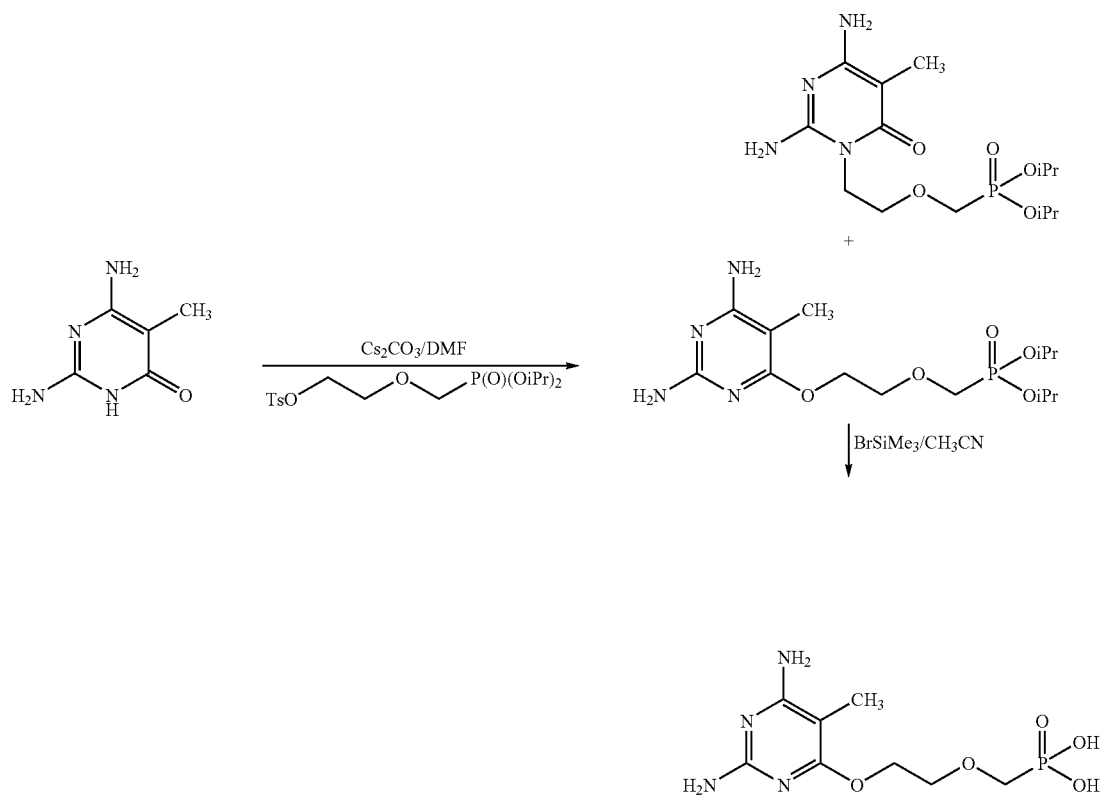

5-Methyl-2,4-diamino-6-hydroxypyrimidine (0.56 g, 4 mmol) was codistilled with toluene and the residue was sonicated with dimethylformamide (7 ml) and cesium carbonate (0.65 g, 2 mmol) and heated to 80° C. 2-[(Diisopropoxyphosphoryl)methoxy]ethyl tosylate (1.7 g, 4.4 mmol, 1.1 eq.) was added, the reaction mixture was heated at 110° C. for 25 h, evaporated in vacuo and codistilled with toluene and ethanol. The residue was treated with hot chloroform, filtered and the filtrate taken down in vacuo. Preparative HPLC afforded N1-isomer (0.39 g, 27%) and O6-isomer (0.61 g, 42%).

and crystallized from water—ethanol to afford product as a white solid: (81 mg, 57%), mp 253–254° C. For $C_8H_{15}N_4O_5P \cdot H_2O$ (296.2) calculated 32.44%; C, 5.78%; H, 18.91%; N, found 32.23%; C, 5.86%; H, 18.56%; N. FABMS: 279 (MH$^+$) (70). $^1$H NMR (D$_2$O+NaOD): 4.37 m, 2H(H-1'); 3.91 m, 2H(H-2'); 3.58 d, 2H, J(P,CH)=8.4 (P—CH$_2$); 1.84 s, 3H(CH$_3$). $^{13}$C NMR: 167.06 (C-6); 163.58 (C-4); 160.01 (C-2); 85.75 (C-5); 70.47 d, J(P,C)=10.3 (C-2'); 68.96 d, J(P,C)=148.9 (P—C); 65.42 (C-1'); 10.54 (CH$_3$).

EXAMPLE 6

5-Phenyl-2,4-diamino-6-[2-(phosphonomethoxy)ethoxy]pyrimidine

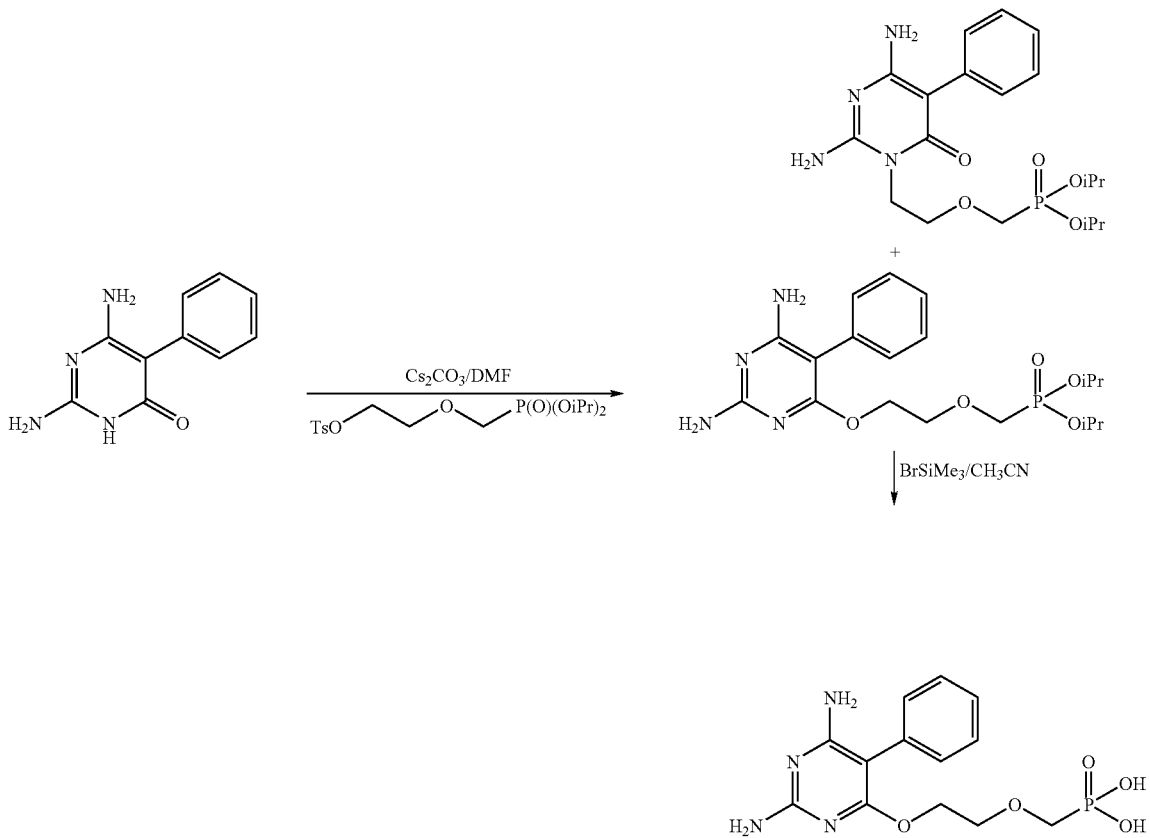

5-Phenyl-2,4-diamino-6-hydroxypyrimidine (0.81 g, 4 mmol) was codistilled with toluene and the residue was sonicated with dimethylformamide (7 ml) and cesium carbonate (0.65 g, 2 mmol) and heated to 80° C. 2-[(Diisopropoxyphosphoryl)methoxy]ethyl tosylate (1.7 g, 4.4 mmol, 1.1 eq.) was added, the reaction mixture was heated at 110° C. for 23 h, evaporated in vacuo and codistilled with toluene and ethanol. The residue was treated with hot chloroform, filtered and the filtrate taken down in vacuo. Preparative HPLC afforded N1-isomer (0.18 g, 10%) and O6-isomer (0.36 g, 21%).

O6-Isomer (5-phenyl-2,4-diamino-6-[2-(diisopropylphosphorylmethoxy)ethoxy]pyrimidine, 0.21 g, 0.5 mmol), acetonitrile (10 ml) and BrSiMe$_3$ (1 ml) was stirred overnight at room temperature. After evaporation in vacuo and codistillation with acetonitrile, the residue was treated with water and conc. aqueous ammonia was added to alkaline reaction. The mixture was evaporated to dryness and the residue was applied onto column of Dowex 50×8 (H$^+$-form, 20 ml) and washed with water. Elution with 2.5% aqueous ammonia and evaporation in vacuo afforded crude product as ammonium salt. This residue in minimum volume of water was applied on Dowex 1×2 (acetate, 25 ml) column, which was then washed with water followed by gradient of acetic acid (0–1 M). The main UV absorbing fraction was evaporated, the residue was 3-times codistilled with water and crystallized from water—ethanol to afford product as a white solid: (133 mg, 75%), mp 230–231° C. For C$_{13}$H$_{17}$N$_4$O$_5$P·3/2H$_2$O (367.3) calculated 42.51%; C, 5.49%; H, 15.25%; N, 8.43%; P, found 42.71%; C, 5.50%; H, 15.27%; N, 8.50%; P. FABMS: 341 (MH$^+$) (40). $^1$H NMR (DMSO-d$_6$): 7.36 m, 2H and 7.25 m, 3H (arom-H); 6.35 brs, 2H and 5.79 brs, 2H(NH$_2$); 4.27 m, 2H(H-1'); 3.65 m, 2H(H-2'); 3.48 d, 2H, J(P,CH)=8.4 (P—CH$_2$).

EXAMPLE 7

5-Cyclopropyl-2,4-diamino-6-[2-(phosphonomethoxy)ethoxy]pyrimidine

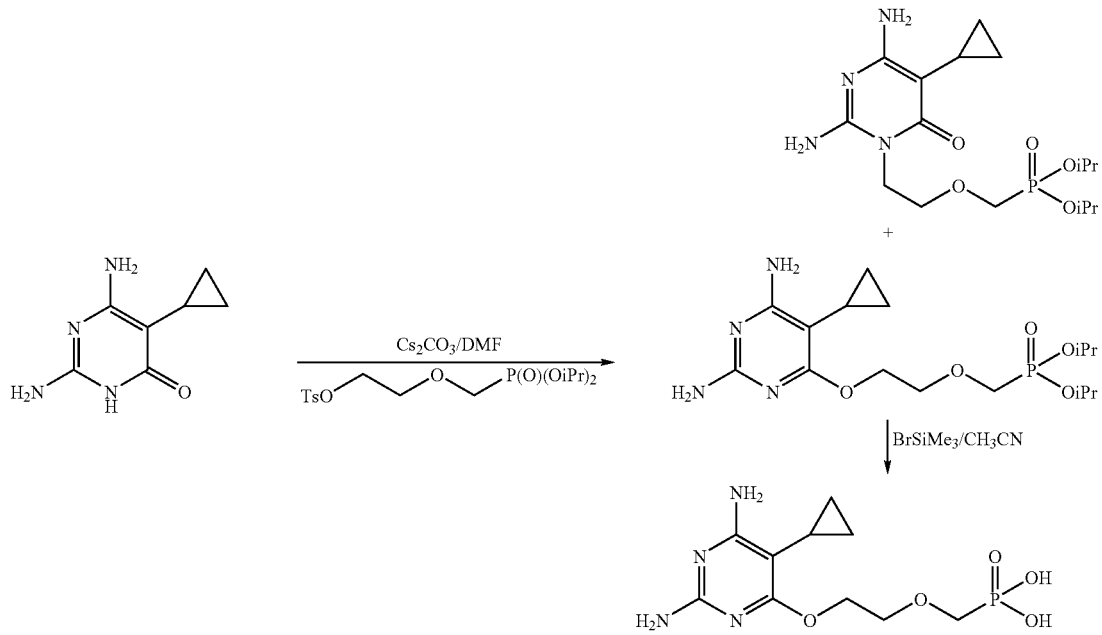

5-Cyclopropyl-2,4-diamino-6-hydroxypyrimidine (0.66 g, 4 mmol) was codistilled with toluene and the residue was sonicated with dimethylformamide (7 ml) and cesium carbonate (0.65 g, 2 mmol) and heated to 80° C. 2-[(Diisopropoxyphosphoryl)methoxy]ethyl tosylate (1.7 g, 4.4 mmol, 1.1 eq.) was added, the reaction mixture was heated at 110° C. for 14 h, evaporated in vacuo and codistilled with toluene and ethanol. The residue was treated with hot chloroform, filtered and the filtrate taken down in vacuo. Preparative HPLC afforded N1-isomer (0.29 g, 19%) and O6-isomer (0.55 g, 35%).

O6-Isomer (5-cyclopropyl-2,4-diamino-6-[2-(diisopropylphosphorylmethoxy)ethoxy]pyrimidine, 0.19 g, 0.5 mmol), acetonitrile (10 ml) and BrSiMe$_3$ (1 ml) was stirred overnight at room temperature. After evaporation in vacuo and codistillation with acetonitrile, the residue was treated with water and conc. aqueous ammonia was added to alkaline reaction. The mixture was evaporated to dryness and the residue was applied onto column of Dowex 50×8 (H$^+$-form, 20 ml) and washed with water. Elution with 2.5% aqueous ammonia and evaporation in vacuo afforded crude product as ammonium salt. This residue in minimum volume of water was applied on Dowex 1×2 (acetate, 25 ml) column, which was then washed with water followed by gradient of acetic acid (0–1 M). The main UV absorbing fraction was evaporated, the residue was 3-times codistilled with water and crystallized from water—ethanol to afford product as a white solid: (125 mg, 82%), mp 255–256° C. For C$_{10}$H$_{17}$N$_4$O$_5$P (304.2) calculated 39.48%; C, 5.63%; H, 18.42%; N, 10.18%; P, found 39.14%; C, 5.63%; H, 18.10%; N, 10.23%; P. FABMS: 305 (MH$^+$) (95). $^1$H NMR (D$_2$O+NaOD): 4.38 m, 2H(H-1'); 3.93 m, 2H(H-2'); 3.62 d, 2H, J(P,CH)=8.4 (P—CH$_2$); 1.24 m, 1H, 0.93 m, 2H and 0.45 m, 2H (cyclopropyl).

EXAMPLE 8

5-Cyano-2,4-diamino-6-[2-(phosphonomethoxy)ethoxy]pyrimidine

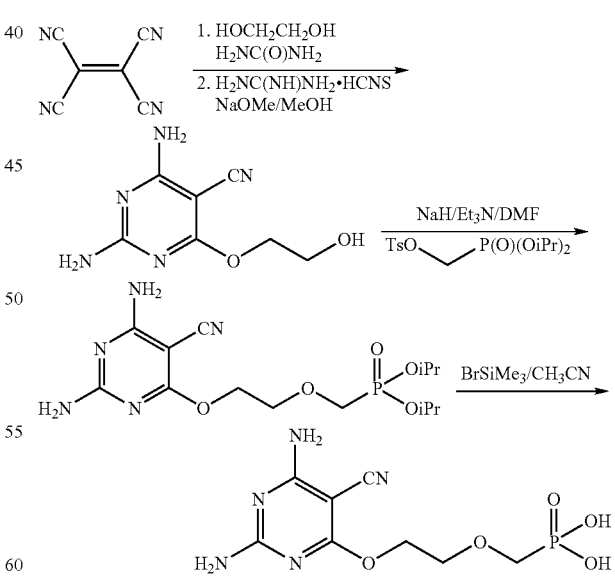

(Reactant 5-cyano-2,4-diamino-6-(2-hydroxyethoxy)pyrimidine was prepared in two steps from tetracyanoethylene: (a) Middleton W. J., Engelhardt V. A.: *J. Am. Chem. Soc.* 1958, 80, 2788. (b) Middleton W. J., Engelhardt V. A.: *J. Am. Chem. Soc.* 1958, 80, 2829.) To the suspension of 5-cyano- 2,4-diamino-6-(2-hydroxyethoxy)pyrimidine (2.4 g, 12 mmol) in triethylamine (8 ml) (diisopropoxyphosphoryl) methyl tosylate (4.8 g, 13.7 mmol) was added followed by dimethylformamide (20 ml) and NaH (60% disp. in mineral oil, 1.3 g). The reaction mixture was stirred at room temperature for 1 h and evaporated in vacuo and codistilled with toluene and ethanol. The residue was chromatographed on silica gel. The fractions eluted with 4% MeOH in $CHCl_3$ gave 2 g (45%) of 5-cyano-2,4-diamino-6-[2-(diisopropoxyphosphorylmethoxy)ethoxy]pyrimidine.

This compound (0.19 g, 0.5 mmol), acetonitrile (10 ml) and $BrSiMe_3$ (1 ml) was stirred overnight at room temperature. After evaporation in vacuo and codistillation with acetonitrile, the residue was treated with water and conc. aqueous ammonia was added to alkaline reaction. The mixture was evaporated to dryness and the residue was applied onto column of Dowex 50×8 ($H^+$-form, 20 ml) and washed with water. Elution with 2.5% aqueous ammonia and evaporation in vacuo afforded crude product as ammonium salt. This residue in minimum volume of water was applied on Dowex 1×2 (acetate, 25 ml) column, which was then washed with water followed by gradient of acetic acid (0–3 M). The main UV absorbing fraction was evaporated, the residue was 3-times codistilled with water and crystallized from water—ethanol to afford product as a white solid: (120 mg, 86%), mp 294–295° C. For $C_8H_{12}N_5O_5P \cdot H_2O$ (307.2) calculated 31.28%; C, 4.59%; H, 22.80%; N, 10.08%; P, found 31.27%; C, 4.67%; H, 22.54%; N, 9.94%; P. FABMS: 290 ($MH^+$) (10). $^1H$ NMR ($D_2O$+NaOD): 4.48 m, 2H(H-1'); 3.95 m, 2H(H-2'); 3.74 d, 2H, J(P,CH)=8.4 (P—$CH_2$). $^{13}C$ NMR: 171.87 (C-6); 166.15 (C-4); 163.30 (C-2); 116.85 (CN); 70.88 d, J(P,C)=10.7 (C-2'); 67.69 d, J(P,C)=156.2 (P—C); 66.72 (C-5); 64.52 (C-1').

EXAMPLE 9

5-Formyl-2,4-diamino-6-[2-(phosphonomethoxy)ethoxy]pyrimidine

5-Cyano-2,4-diamino-6-[2-(diisopropoxyphosphorylmethoxy)ethoxy]pyrimidine (1.5 g, 4 mmol) was hydrogenated in water (36 ml) and sulfuric acid (6 ml) over 5% palladium on charcoal (0.25 g) under stirring for 20 h at room temperature. The mixture was filtered through a pad of Celite and the catalyst was washed with hot water and hot methanol (100 ml each). The filtrate was neutralized with aqueous NaOH and solvents evaporated. The residue was mixed with hot methanol, salts were filtered off and the mixture was taken down. Product was purified by column chromatography on silica gel (elution with 3% MeOH in $CHCl_3$) to give 0.63 g (42%) of 5-formyl-2,4-diamino-6-[2-(diisopropoxyphosphorylmethoxy)ethoxy]pyrimidine.

This compound (0.36 g, 0.95 mmol), acetonitrile (10 ml) and $BrSiMe_3$ (1 ml) was stirred for 2.5 h at room temperature. After evaporation in vacuo and codistillation with acetonitrile, the residue was treated with water and triethylamine was added to alkaline reaction. The mixture was evaporated to dryness and the residue was applied onto column of Dowex 1×2 (acetate, 25 ml) column, which was then washed with water followed by gradient of acetic acid (0–2 M). The main UV absorbing fraction was evaporated, the residue was 3-times codistilled with water and crystallized from water—methanol to afford product as a white solid: (230 mg, 82%), mp 225–227° C. For $C_8H_{13}N_4O_6P \cdot 5/4 H_2O$ (314.7) calculated 30.53%; C, 4.96%; H, 17.80%; N, found 30.87%; C, 5.01%; H, 17.65%; N.

FABMS: 293 ($MH^+$) (10). $^1H$ NMR ($D_2O$+NaOD): 9.73 s, 1H(CH=O); 4.46 m, 2H(H-1'); 3.95 m, 2H(H-2'); 3.59 d, 2H, J(P,CH)=8.4 (P—$CH_2$). $^{13}C$ NMR: 187.89 (CH=O); 172.46 (C-6); 164.285 (C-4); 163.85 (C-2); 92.44 (C-5); 70.25 d, J(P,C)=9.3 (C-2'); 69.18 d, J(P,C)=148.4 (P—C); 66.11 (C-1').

EXAMPLE 10

Viruses

The origins of MSV, HIV type 1 (HIV-1) (strain $III_B$ and Ba-L), HIV-2 (strain ROD) and FIV (strain Petaluma) have been described previously (Balzarini et al., AIDS 5: 21–28, 1991; De Clercq et al., Proc. Soc. Exp. Biol. Med. 137: 590–594, 1971; Egberink et al., Proc. Natl. Acad. Sci. 87:3087–3091, 1990; Hartmann et al., Antiviral Chem. Chemother. 5:13–19, 1994; Popovic et al., Science 224: 497–500, 1984). HIV-1($III_B$) and HIV-2(ROD) stocks were obtained from supernatants of virus-infected MT-4 cell cultures. HIV-1$_{BaL}$ was expanded in human primary M/M, whose supernatants were collected, filtered and stored at

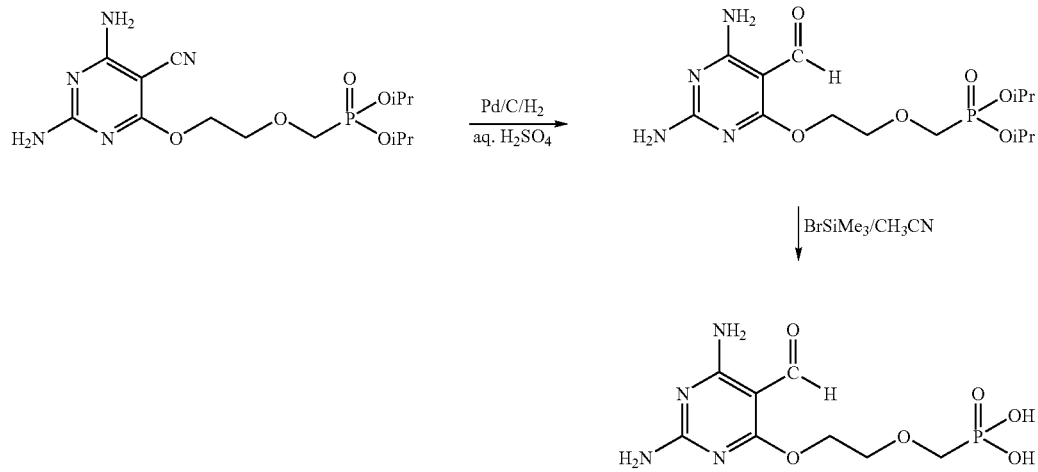

−80° C. before use. Characteristics of viral stocks used for this study were 2.1×10⁸ HIV-RNA genomes/ml (corresponding to 35 ng of p24 antigen) and 5,000 tissue culture infectious doses 50% per ml ($TCID_{50}$/ml) as assessed by virus titration in other primary M/M cultures. The isolation and characterization of the clinical HIV-1 isolates L1S, L6S and L6S/PMEA has been reported (Thormar et al., Proc. Natl. Acad. Sci. USA 93:3283–3287, 1995; Van Laethem et al., AIDS 15:553–561, 2001). The HIV-1/L1S clinical isolate was derived from a patient not treated with NRTIs (nucleoside reverse transcriptase inhibitors) or ANPs and cultured without the selective pressure of any drugs. Therefore, it contained no obvious mutations that are characteristic for NRTI- or ANP-treated patients. HIV-1/L6S is a clinical isolate from a drug-treated individual cultured without the selective pressure of any drugs. As is characteristic for NRTI-treated patients, it contained S68G, K70T, V75I, F77L, F116Y and Q151M mutations in its RT. HIV-1/L6S/PMEA is the clinical isolate HIV-1/L6S that has been isolated after culturing the virus for 11 passages in the presence of increasing concentrations of PMEA (adefovir). It gained, in addition to the mutations mentioned for HIV-1/L6S, also the PMEA-characteristic K65R mutation in its reverse transcriptase (RT).

EXAMPLE 11

Antiviral Activity of the Compounds of the Invention

The antiviral activities of compounds herein were determined in accord with the general procedures disclosed in J. Balzarini, et al. "9-(2-phosphonylmethoxyethyl)adenine (PMEA) effectively inhibits retrovirus replication in vitro and simian immunodeficiency virus infection in rhesus monkeys" *AIDS* 5:21–28, 1991 and J. Balzarini, et al. "Differential antiherpesvirus and antiretrovirus effects of the (S) and (R) enantiomers of acyclic nucleoside phosphonates: potent and selective in vitro and in vivo antiretrovirus activities of (R)-9-(2-phosphonomethoxypropyl)-2,6-diaminopurine" *Antimicrobial Agents and Chemotherapy*, 37:332–338, 1993.

A variety of 5-substituted 2,4-diamino-6-[2-(phosphonomethoxy)ethoxy]pyrimidines were investigated for their inhibitory activity against a panel of DNA and retroviruses. None of the compounds were active against herpes simplex virus type 1 and type 2, cytomegalovirus and vaccinia virus. 5-Methyl-2,4-diamino-6-[2-(phosphonomethoxy)ethoxy]pyrimidine (Example 5) showed moderate anti-VZV activity. However, several compounds were markedly inhibitory against murine (MSV) and human (HIV-1, HIV-2) retroviruses. The 5-cyano and 5-formyl derivatives (Examples 8 and 9, respectively) were inhibitory against HIV at 0.8 to 3.3 μg/ml, and against MSV at 2.7 to 6 μg/ml (Table). These antiviral potencies were comparable with those found for the 5-unsubstituted 2,4-diamino-6-[2-(phosphonomethoxy)ethoxy]pyrimidine and the 5-chloro derivative against HIV but inferior for MSV. Interestingly, the 5-methyl derivative proved exquisitely inhibitory not only against MSV ($EC_{50}$: 0.04–0.06 μg/ml) but also against HIV-1 and HIV-2 ($EC_{50}$: 0.065 μg/ml). In contrast with the 5-unsubstituted compound whose anti-HIV activity was 20-fold less potent than its anti-MSV activity, 5-methyl derivative (Example 5) showed comparable anti-HIV and -MSV activity. As a consequence, this activity against HIV was more pronounced than observed for any other acyclic nucleoside phosphonate derivative ever tested. Therefore, it cannot be excluded that this compound exerts also superior anti-HIV activity in HIV-infected individuals compared with the reference drugs PMEA (adefovir) and (R)-PMPA (tenofovir). This compound, however, proved also slightly more cytostatic in CEM cell cultures ($CC_{50}$: 1.3–4.1 μg/ml) than PMEA ($CC_{50}$: 11 μg/ml) (Table).

The 5-cyano (Example 8), 5-methyl (Example 5) and 5-chloro-2,4-diamino-6-[2-(phosphonomethoxy)ethoxy]pyrimidine were also evaluated for their antiretroviral activity in MSV-infected newborn NMRI mice in comparison with PMEA and (R)-PMPA. The order of antiviral efficacy was from the 5-cyano derivative (being the least effective agent) over the 5-chloro derivative, to the 5-methyl derivative (being the most effective agent). 5-Cyano-2,4-diamino-6-[2-(phosphonomethoxy)ethoxy]pyrimidine prevented MSV-induced tumor cell formation and associated animal death in a less efficient way than PMEA. Also, the 5-chloro-2,4-diamino-6-[2-(phosphonomethoxy)ethoxy]pyrimidine was inferior to PMEA for both initiation of MSV-induced tumor formation and MSV-associated animal death (Table). However, the 5-methyl derivative was clearly superior to PMEA, but also to (R)-PMPA. At 50 and 20 mg/kg tumor formation was completely prevented by 5-methyl-2,4-diamino-6-[2-(phosphonomethoxy)ethoxy]pyrimidine, PMEA and (R)-PMPA. At 5 mg/kg, 90% of mice were free from tumor formation in the presence of 5-methyl derivative, compared with 70% and 10% in the presence of PMEA and (R)-PMPA. However, the highest dose of 5-methyl-2,4-diamino-6-[2-(phosphonomethoxy)ethoxy]pyrimidine (50 mg/kg) demonstrated animal death (average: 10.1 days) in tumor-free mice, presumably due to drug toxicity. This phenomenon was also seen with PMEA at 50 and 20 mg/kg, but not with (R)-PMPA at 50 mg/kg. Thus, whereas 5-methyl derivative was slightly more effective in prevention of MSV-induced tumor formation than (R)-PMPA and clearly more effective than PMEA, it was also slightly more toxic. Therefore, both drugs likely have a comparable antiretroviral selectivity in vivo.

Inhibitory activity of test compounds against MSV-induced tumor cell formation in newborn NMRI mice

| | Dose[a] | Mean day of tumor initiation (% tumor free on day 12) | Mean day of animal death (% survivors on day 12) | Number of mice |
|---|---|---|---|---|
| Example | | | | |
| 8 | 50 mg/kg | 8.20 ± 1.62 | >12 (100%) | 10 |
| | 20 | 7.20 ± 1.03 | 11.5 ± 0.58 (60%) | 10 |
| | 5 | 6.40 ± 0.70 | 10.9 ± 0.57 | 10 |
| 5 | 50 mg/kg | >12 (100%) | 10.1 ± 1.10[b] | 10 |
| | 20 | >12 (100%) | >12 (100%) | 10 |
| | 5 | 8.0 (90%) | >12 (100%) | 10 |
| Reference compounds | | | | |
| 5-Cl | 50 mg/kg | 8.76 ± 1.86 (15%) | >12 (100%) | 20 |
| | 20 | 7.44 ± 1.42 (10%) | 11.8 ± 0.50 (80%) | 20 |
| | 5 | 6.70 ± 0.80 | 11.5 ± 0.69 (45%) | 20 |
| PMEA | 50 mg/kg | >12 (100%) | 8.80 ± 0.63[b] | 10 |
| | 20 | >12 (100%) | 9.0 (90%)[b] | 10 |
| | 5 | 9.33 ± 0.58 (70%) | >12 (100%) | 10 |

| | Dose[a] | Mean day of tumor initiation (% tumor free on day 12) | Mean day of animal death (% survivors on day 12) | Number of mice |
|---|---|---|---|---|
| (R)-PMPA | 50 mg/kg | >12 (100%) | >12 (100%) | 20 |
| | 20 | >12 (100%) | >12 (100%) | 20 |
| | 5 | 10.5 ± 2.12 (10%) | >12 (100%) | 20 |
| Control | | 5.03 ± 0.73 | 10.9 ± 0.74 | 29 |

[a]Compound was injected i.p. at days 1, 2, 3, 4 and 5. Virus was injected i.m. at day 1.
[b]Animal death occurred in a number of mice, due to drug toxicity.

We claim:

1. A compound of the formula (I):

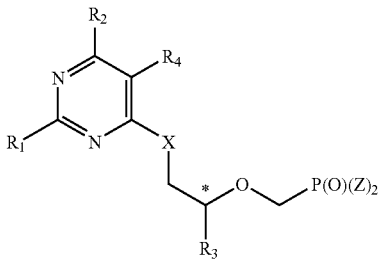

wherein

* designates a chiral carbon atom;
$R_1$ is H, amino, or methylsulfanyl;
$R_2$ is H, methyl, halo, —$N(R_5)_2$, hydroxy, or protected hydroxy;
$R_3$ is independently methyl, hydroxymethyl, halomethyl, or protected hydroxymethyl;
$R_4$ is selected from:
(i) $C_1$ to $C_{10}$ alkyl,
(ii) $C_2$ to $C_{10}$ alkenyl, or,
(iii) $C_2$ to $C_{10}$ alkynyl,
(iv) $C_3$–$C_8$ cycloalkyl,
(v) aryl,
(vi) heteroaryl,
(vii) $C_7$–$C_{14}$ arylalkyl,
(viii) heteroarylalkyl,
(ix) —$CH_2OH$,
(x) —$CH_2OR_5$
(xi) —$CH_2C(O)R_5$,
(xii) —$CH_2R_6$,
(xiii) —$CH_2OC(O)R_5$
(xiv) —$CH_2OC(O)CH(R_7)(NHR_8)$,
(xv) —$CH_2NR_9R_{10}$,
(xvi) —$CH_2CN$,
(xvii) —$CO_2R_5$
(xviii) —$CH_2CH_2OH$,
(xix) —$CH_2CH_2OR_5$
(xx) —$CH_2CH_2OC(O)R_5$
(xxi) —$CH_2CH_2OC(O)CH(R_7)(NHR_8)$,
(xxii) —$CH_2SH$,
(xxiii) —$C(O)H$,
(xxiv) —$CH_2CO_2R_9$,
(xxv) —$CH_2SO_3H$,
(xxvi) —$CH_2CH_2SO_3H$,
(xxvii) —$CH_2CH_2PO_3H_2$,
(xxviii) —$CH_2CH_2OCH_2PO_3H_2$,
(xxix) —$CH_2OPO_3H_2$,
(xxx) —$OCH_2PO_3H_2$,
(xxxi) —OH,
(xxxii) —$OR_{10}$,
(xxxiii) —$NH_2$,
(xxxiv) —$NR_{11}R_{12}$,
(xxxv) —SH,
(xxxvi) —$SR_5$,
(xxxvii) —SCN,
(xxxviii) —$N_3$,
(xxxix) —CN,
(xl) —$CONR_{11}R_{12}$
(xli) —$CH_2CONR_{11}R_{12}$
(xlii) —NHOH,
(xliii) —$NHOR_5$,
(xliv) —NO,
(xlv) —$NO_2$,
(xlvi) —$NHNR_{11}R_{12}$
(xlvii) 2-halovinyl,
(xlviii) 3,3,3-trifluoropropenyl,
(xlix) $C_1$–$C_{10}$ 2-(alkoxycarbonyl)ethenyl,
(l) 2-carboxyethenyl,
(li) 2-cyanoethenyl,
(lii) difluoromethyl,
(liii) trifluoromethyl,
(liv) 2,2,2-trifluoroethyl,
(lv) 2-haloethyl; and
(lvi) —$CH_2N_3$;
X independently is oxygen, sulfur, or a bond;
Z independently is hydroxy, an ester or amide;
$R_5$ is independently H, $C_1$–$C_{10}$ alkyl or a protecting group;
$R_6$ is F, Cl, Br or I;
$R_7$ is the side chain of any of the unprotected or N-protected α-amino acids;
$R_8$ is H or —$C(O)CH(R_7)(NH_2)$;
$R_9$ and $R_{10}$ are independently selected from H, $C_1$–$C_{10}$ alkyl, carboxyalkyl, aminoalkyl, and $C_2$–$C_{10}$ alkenyl, or both together form a cycle with or without participation of heteroatom; and
$R_{11}$ and $R_{12}$ are independently selected from H, $C_1$ to $C_{10}$ alkyl, $C_3$–$C_8$ cycloalkyl, heteroaryl and $C_7$–$C_{12}$ arylalkyl, or both together form a cycle with or without participation of heteroatom; and
salts and solvates thereof.

2. The compound of claim 1 wherein $R_1$ and $R_2$ are amino and X is oxygen.

3. The compound of claim 1 wherein $R_1$ and $R_2$ are simultaneously amino, $R_3$ is methyl, X is oxygen and the $R_3$ configuration is (R).

4. The compound of claim 1 wherein $R_1$ and $R_2$ are simultaneously amino, $R_3$ is hydroxymethyl, X is oxygen and the $R_3$ configuration is (R).

5. The compound of claim 1 wherein $R_1$ and $R_2$ are simultaneously amino and X is sulfur.

6. The compound of claim 1 wherein $R_1$ is amino, $R_2$ is hydroxy and X is oxygen.

7. The compound of claim 1 which is crystalline.

8. The compound of claim 1 which is a substantially pure enantiomer at the chiral carbon.

9. The compound of claim 8 which is in the (R) configuration.

10. The compound of claim 8 which is in the (S) configuration.

11. A compound of the formula (Iaa):

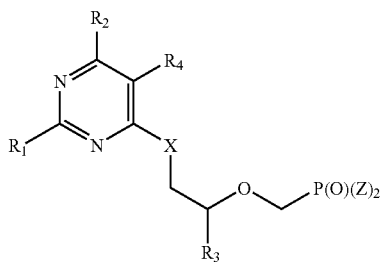

wherein
R₁ is H, amino, or methylsulfanyl;
R₂ is H, methyl, halo, —N(R₅)₂, hydroxy, or protected hydroxy;
R₃ is independently H, methyl, hydroxymethyl, halomethyl, or protected hydroxymethyl;
R₄ is selected from:
(i) $C_1$ to $C_{10}$ alkyl,
(ii) $C_2$ to $C_{10}$ alkenyl, or,
(iii) $C_2$ to $C_{10}$ alkynyl,
(iv) $C_3$–$C_8$ cycloalkyl,
(v) aryl,
(vi) heteroaryl,
(vii) $C_7$–$C_{14}$ arylalkyl,
(viii) heteroarylalkyl,
(ix) —CH₂OH,
(x) —CH₂OR₅,
(xi) —CH₂C(O)R₅,
(xii) —CH₂R₆,
(xiii) —CH₂OC(O)R₅
(xiv) —CH₂OC(O)CH(R₇)(NHR₈),
(xv) —CH₂NR₉R₁₀,
(xvi) —CH₂CN,
(xvii) —CO₂R₅
(xviii) —CH₂CH₂OH,
(xix) —CH₂CH₂OR₅
(xx) —CH₂CH₂OC(O)R₅
(xxi) —CH₂CH₂OC(O)CH(R₇)(NHR₈),
(xxii) —CH₂SH,
(xxiii) —C(O)H,
(xxiv) —CH₂CO₂R₉,
(xxv) —CH₂SO₃H,
(xxvi) —CH₂CH₂SO₃H,
(xxvii) —CH₂CH₂PO₃H₂,
(xxviii) —CH₂CH₂OCH₂PO₃H₂,
(xxix) —CH₂OPO₃H₂,
(xxx) —OCH₂PO₃H₂,
(xxxi) —OH,
(xxxii) —OR₁₀
(xxxiii) —NH₂,
(xxxiv) —NR₁₁R₁₂,
(xxxv) —SH,
(xxxvi) —SR₅,
(xxxvii) —SCN,
(xxxviii) —N₃,
(xxxix) —CN,
(xl) —CONR₁₁R₁₂
(xli) —CH₂CONR₁₁R₁₂
(xlii) —NHOH,
(xliii) —NHOR₅,
(xliv) —NO,
(xlv) —NO₂,
(xlvi) —NHNR₁₁R₁₂
(xlvii) 2-halovinyl,
(xlviii) 3,3,3-trifluoropropenyl,
(xlix) $C_1$–$C_{10}$ 2-(alkoxycarbonyl)ethenyl,
(l) 2-carboxyethenyl,
(li) 2-cyanoethenyl,
(lii) difluoromethyl,
(liii) trifluoromethyl,
(liv) 2,2,2-trifluoroethyl,
(lv) 2-haloethyl; and
(lvi) —CH₂N₃;

X independently is oxygen, sulfur, or a bond;
Z independently is hydroxy, an ester or amide;
R₅ is independently H, $C_1$–$C_{10}$ alkyl or a protecting group;
R₆ is F, Cl, Br or I;
R₇ is the side chain of any of the unprotected or N-protected α-amino acids;
R₈ is H or —C(O)CH(R₇)(NH₂);
R₉ and R₁₀ are independently selected from H, $C_1$–$C_{10}$ alkyl, carboxyalkyl, aminoalkyl, and $C_2$–$C_{10}$ alkenyl, or both together form a cycle with or without participation of heteroatom; and
R₁₁, and R₁₂ are independently selected from H, $C_1$ to $C_{10}$ alkyl, $C_3$–$C_8$ cycloalkyl, heteroaryl and $C_7$–$C_{12}$ arylalkyl, or both together form a cycle with or without participation of heteroatom: and
salts and solvates thereof.

12. The compound of claim 11 wherein R₁ and R₂ are amino, R₃ is hydrogen and X is oxygen.

13. The compound of claim 11 wherein R₁ and R₂ are simultaneously amino, R₃ is hydrogen and X is sulfur.

14. The compound of claim 11 wherein R₁ is amino, R₂ is hydroxy, R₃ is hydrogen and X is oxygen.

15. A composition comprising a pharmaceutically acceptable excipient and a compound of claim 1.

16. A method of preparation of compounds of formula (I)

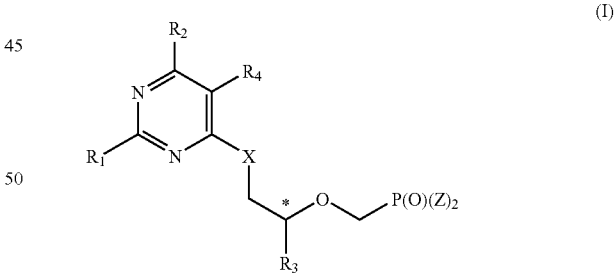

comprising reacting a compound of formula (II):

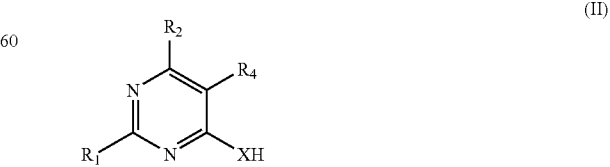

with a compound of the formula (III):

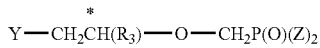

(III)

where Y is a leaving group;
in dipolar aprotic solvent in the presence of a base;
wherein * designates a chiral carbon atom;
$R_1$ is H, amino, or methylsulfanyl;
$R_2$ is H, methyl, halo, —$N(R_5)_2$, hydroxy, protected hydroxy or a group of the formula (Ia)

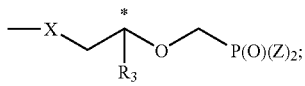

(Ia)

$R_3$ is independently methyl, hydroxymethyl, halomethyl, or protected hydroxymethyl;
$R_4$ is selected from:
(i) $C_1$ to $C_{10}$ alkyl,
(ii) $C_2$ to $C_{10}$ alkenyl, or,
(iii) $C_2$ to $C_{10}$ alkynyl,
(iv) $C_3$–$C_8$ cycloalkyl,
(v) aryl,
(vi) heteroaryl,
(vii) $C_7$–$C_{14}$ arylalkyl,
(viii) heteroarylalkyl,
(ix) —$CH_2OH$,
(x) —$CH_2OR_5$,
(xi) —$CH_2C(O)R_5$,
(xii) —$CH_2R_6$,
(xiii) —$CH_2OC(O)R_5$
(xiv) —$CH_2OC(O)CH(R_7)(NHR_8)$,
(xv) —$CH_2NR_9R_{10}$,
(xvi) —$CH_2CN$,
(xvii) —$CO_2R_5$
(xviii) —$CH_2CH_2OH$,
(xix) —$CH_2CH_2OR_5$
(xx) —$CH_2CH_2OC(O)R_5$
(xxi) —$CH_2CH_2OC(O)CH(R_7)(NHR_8)$,
(xxii) —$CH_2SH$,
(xxiii) —$C(O)H$,
(xxiv) —$CH_2CO_2R_9$,
(xxv) —$CH_2SO_3H$,
(xxvi) —$CH_2CH_2SO_3H$,
(xxvii) —$CH_2CH_2PO_3H_2$,
(xxviii) —$CH_2CH_2OCH_2PO_3H_2$,
(xxix) —$CH_2OPO_3H_2$,
(xxx) —$OCH_2PO_3H_2$,
(xxxi) —OH,
(xxxii) —$OR_{10}$
(xxxiii) —$NH_2$,
(xxxiv) —$NR_{11}R_{12}$,
(xxxv) —SH,
(xxxvi) —$SR_5$,
(xxxvii) —SCN,
(xxxviii) —$N_3$,
(xxxix) —CN,
(xl) —$CONR_{11}R_{12}$
(xli) —$CH_2CONR_{11}R_{12}$
(xlii) —NHOH,
(xliii) —$NHOR_5$,
(xliv) —NO,
(xlv) —$NO_2$,
(xlvi) —$NHNR_{11}R_{12}$ (xlvii) 2-halovinyl,
(xlviii) 3,3,3-trifluoropropenyl,
(xlix) $C_1$–$C_{10}$ 2-(alkoxycarbonyl)ethenyl,
(l) 2-carboxyethenyl,
(li) 2-cyanoethenyl,
(lii) difluoromethyl,
(liii) trifluoromethyl,
(liv) 2,2,2-trifluoroethyl,
(lv) 2-haloethyl; and
(lvi) —$CH_2N_3$;
X is O or S;
Z independently is hydroxy, an ester or amide;
$R_5$ is independently H, $C_1$–$C_{10}$ alkyl or a protecting group;
$R_6$ is F, Cl, Br or I;
$R_7$ is the side chain of any of the unprotected or N-protected α-amino acids;
$R_8$ is H or —$C(O)CH(R_7)(NH_2)$;
$R_9$ and $R_{10}$ are independently selected from H, $C_1$–$C_{10}$ alkyl, carboxyalkyl, aminoalkyl, and $C_2$–$C_{10}$ alkenyl, or both together form a cycle with or without participation of heteroatom; and
$R_{11}$ and $R_{12}$ are independently selected from H, $C_1$ to $C_{10}$ alkyl, $C_3$–$C_8$ cycloalkyl, heteroaryl and $C_7$–$C_{12}$ arylalkyl, or both together form a cycle with or without participation of heteroatom.

17. The method of claim 16 further comprising isolating the resulting compound of the formula (I).

18. The method of claim 16 wherein Z is ester or amide and additionally hydrolyzing one or both Z groups to produce the compound of formula (I) where at least one Z is hydroxy.

19. The method of claim 16 where Z is $(OR_4)_2$ and $R_4$ is isopropyl.

20. The method of claim 16 where $R_3$ is methyl and Y is p-toluenesulfonyloxy or bromo.

21. A method of preparation of compounds of formula (Iaa)

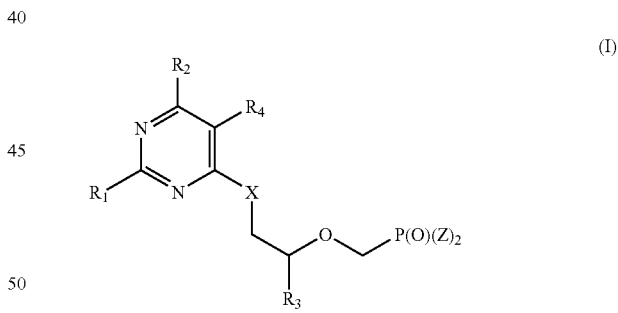

(I)

comprising reacting a compound of formula (II):

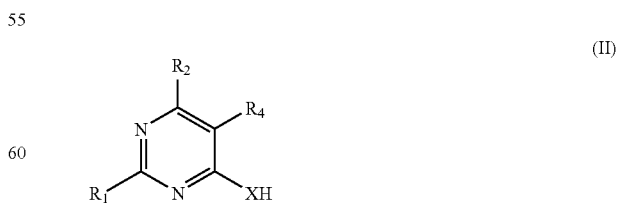

(II)

with a compound of the formula (III):

Y—$CH_2CH(R_3)$—O—$CH_2P(O)(Z)_2$ (III)

where Y is a leaving group;

in dipolar aprotic solvent in the presence of a base;
wherein
$R_1$ is H, amino, or methylsulfanyl;
$R_2$ is H, methyl, halo, —$N(R_5)_2$, hydroxy, protected hydroxy or a group of the formula (Ia)

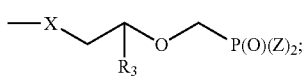

$R_3$ is independently H, methyl, hydroxymethyl, halomethyl, or protected hydroxymethyl;
$R_4$ is selected from:
(i) $C_1$ to $C_{10}$ alkyl,
(ii) $C_2$ to $C_{10}$ alkenyl, or,
(iii) $C_2$ to $C_{10}$ alkynyl,
(iv) $C_3$–$C_8$ cycloalkyl,
(v) aryl,
(vi) heteroaryl,
(vii) $C_7$–$C_{14}$ arylalkyl,
(viii) heteroarylalkyl,
(ix) —$CH_2OH$,
(x) —$CH_2OR_5$
(xi) —$CH_2C(O)R_5$,
(xii) —$CH_2R_6$,
(xiii) —$CH_2OC(O)R_5$
(xiv) —$CH_2OC(O)CH(R_7)(NHR_8)$,
(xv) —$CH_2NR_9R_{10}$,
(xvi) —$CH_2CN$,
(xvii) —$CO_2R_5$
(xviii) —$CH_2CH_2OH$,
(xix) —$CH_2CH_2OR_5$
(xx) —$CH_2CH_2OC(O)R_5$
(xxi) —$CH_2CH_2OC(O)CH(R_7)(NHR_8)$,
(xxii) —$CH_2SH$,
(xxiii) —$C(O)H$,
(xxiv) —$CH_2CO_2R_9$,
(xxv) —$CH_2SO_3H$,
(xxvi) —$CH_2CH_2SO_3H$,
(xxvii) —$CH_2CH_2PO_3H_2$,
(xxviii) —$CH_2CH_2OCH_2PO_3H_2$,
(xxix) —$CH_2OPO_3H_2$,
(xxx) —$OCH_2PO_3H_2$,
(xxxi) —OH,
(xxxii) —$OR_{10}$
(xxxiii) —$NH_2$,
(xxxiv) —$NR_{11}R_{12}$,
(xxxv) —SH,
(xxxvi) —$SR_5$,
(xxxvii) —SCN,
(xxxviii) —$N_3$,
(xxxix) —CN,
(xl) —$CONR_{11}R_{12}$
(xli) —$CH_2CONR_{11}R_{12}$
(xlii) —NHOH,
(xliii) —$NHOR_5$,
(xliv) —NO,
(xlv) —$NO_2$,
(xlvi) —$NHNR_{11}R_{12}$
(xlvii) 2-halovinyl,
(xlviii) 3,3,3-trifluoropropenyl,
(xlix) $C_1$–$C_{10}$ 2-(alkoxycarbonyl)ethenyl,
(l) 2-carboxyethenyl,
(li) 2-cyanoethenyl,
(lii) difluoromethyl,
(liii) trifluoromethyl,
(liv) 2,2,2-trifluoroethyl,
(lv) 2-haloethyl; and
(lvi) —$CH_2N_3$;
X is O or S;
Z independently is hydroxy, an ester or amide;
$R_5$ is independently H, $C_1$–$C_{10}$ alkyl or a protecting group;
$R_6$ is F, Cl, Br or I;
$R_7$ is the side chain of any of the unprotected or N-protected α-amino acids;
$R_8$ is H or —$C(O)CH(R_7)(NH_2)$;
$R_9$ and $R_{10}$ are independently selected from H, $C_1$–$C_{10}$ alkyl, carboxyalkyl, aminoalkyl, and $C_2$–$C_{10}$ alkenyl, or both together form a cycle with or without participation of heteroatom; and
$R_{11}$ and $R_{12}$ are independently selected from H, $C_1$ to $C_{10}$ alkyl, $C_3$–$C_8$ cycloalkyl, heteroaryl and $C_7$–$C_{12}$ arylalkyl, or both together form a cycle with or without participation of heteroatom.

22. A method for the preparation of compounds of formula (I):

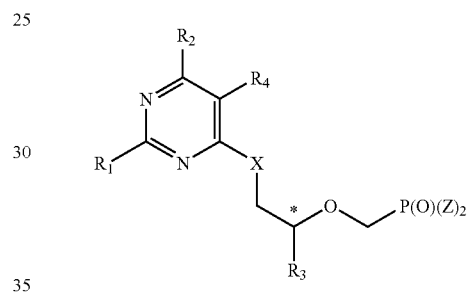

where $R_2$ of formula (I) is —$N(R_5)_2$;
comprising reacting a compound (IV)

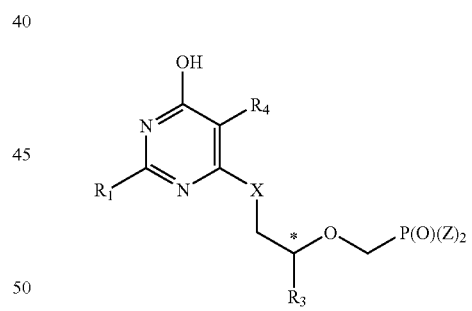

with an amine $HN(R_5)_2$;
wherein:
* designates a chiral carbon atom;
$R_1$ is H, amino or methylsulfanyl;
$R_3$ is independently methyl, hydroxymethyl, halomethyl or protected hydroxymethyl;
$R_4$ is selected from:
(i) $C_1$ to $C_{10}$ alkyl,
(ii) $C_2$ to $C_{10}$ alkenyl, or,
(iii) $C_2$ to $C_{10}$ alkynyl,
(iv) $C_3$–$C_8$ cycloalkyl,
(v) aryl,
(vi) heteroaryl,
(vii) $C_7$–$C_{14}$ arylalkyl,
(viii) heteroarylalkyl, (ix) —CH$_2$OH,
(x) —CH$_2$OR$_5$,
(xi) —CH$_2$C(O)R$_5$,
(xii) —CH$_2$R$_6$,
(xiii) —CH$_2$OC(O)R$_5$,
(xiv) —CH$_2$OC(O)CH(R$_7$)(NHR$_8$),
(xv) —CH$_2$NR$_9$R$_{10}$,
(xvi) —CH$_2$CN,
(xvii) —CO$_2$R$_5$,
(xviii) —CH$_2$CH$_2$OH,
(xix) —CH$_2$CH$_2$OR$_5$,
(xx) —CH$_2$CH$_2$OC(O)R$_5$,
(xxi) —CH$_2$CH$_2$OC(O)CH(R$_7$)(NHR$_8$),
(xxii) —CH$_2$SH,
(xxiii) —C(O)H,
(xxiv) —CH$_2$CO$_2$R$_9$,
(xxv) —CH$_2$SO$_3$H,
(xxvi) —CH$_2$CH$_2$SO$_3$H,
(xxvii) —CH$_2$CH$_2$PO$_3$H$_2$,
(xxviii) —CH$_2$CH$_2$OCH$_2$PO$_3$H$_2$,
(xxix) —CH$_2$OPO$_3$H$_2$,
(xxx) —OCH$_2$PO$_3$H$_2$,
(xxxi) —OH,
(xxxii) —OR$_{10}$
(xxxiii) —NH$_2$,
(xxxiv) —NR$_{11}$R$_{12}$,
(xxxv) —SH,
(xxxvi) —SR$_5$,
(xxxvii) —SCN,
(xxxviii) —N$_3$,
(xxxix) —CN,
(xl) —CONR$_{11}$R$_{12}$
(xli) —CH$_2$CONR$_{10}$R$_{12}$
(xlii) —NHOH,
(xliii) —NHOR$_5$,
(xliv) —NO,
(xlv) —NO$_2$,
(xlvi) —NHNR$_{11}$R$_{12}$
(xlvii) 2-halovinyl,
(xlviii) 3,3,3-trifluoropropenyl,
(xlix) C$_1$–C$_{10}$ 2-(alkoxycarbonyl)ethenyl,
(l) 2-carboxyethenyl,
(li) 2-cyanoethenyl,
(lii) difluoromethyl,
(liii) trifluoromethyl,
(liv) 2,2,2-trifluoroethyl,
(lv) 2-haloethyl; and
(lvi) —CH$_2$N$_3$;

X is O or S;
Z independently is hydroxy, an ester or amide; and
R$_5$ is independently H, C$_1$–C$_8$ alkyl or a protecting group.

23. The method of claim 22 further comprising hydrolyzing one or both Z groups to produce the compound of formula (I) where one or both of Z are hydroxyl.

24. A method for the preparation of compounds of formula (Iaa):

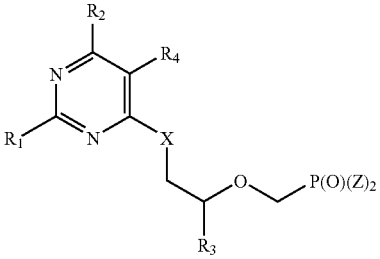

(Iaa)

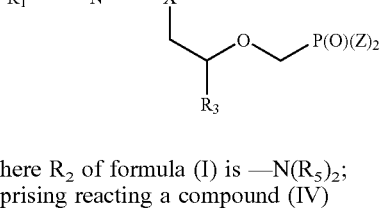

where R$_2$ of formula (I) is —N(R$_5$)$_2$;
comprising reacting a compound (IV)

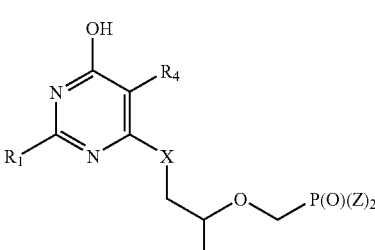

(IV)

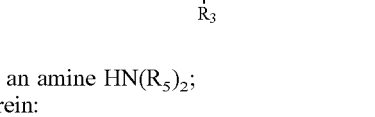

with an amine HN(R$_5$)$_2$;
wherein:
R$_1$ is H, amino or methylsulfanyl;
R$_3$ is independently H, methyl, hydroxymethyl, halomethyl or protected hydroxymethyl;
R$_4$ is selected from:
(i) C$_1$ to C$_{10}$ alkyl,
(ii) C$_2$ to C$_{10}$ alkenyl, or,
(iii) C$_2$ to C$_{10}$ alkynyl,
(iv) C$_3$–C$_8$ cycloalkyl,
(v) aryl,
(vi) heteroaryl,
(vii) C$_7$–C$_{14}$ arylalkyl,
(viii) heteroarylalkyl,
(ix) —CH$_2$OH,
(x) —CH$_2$OR$_5$,
(xi) —CH$_2$C(O)R$_5$,
(xii) —CH$_2$R$_6$,
(xiii) —CH$_2$OC(O)R$_5$
(xiv) —CH$_2$OC(O)CH(R$_7$)(NHR$_8$),
(xv) —CH$_2$NR$_9$R$_{10}$,
(xvi) —CH$_2$CN,
(xvii) —CO$_2$R$_5$
(xviii) —CH$_2$CH$_2$OH,
(xix) —CH$_2$CH$_2$OR$_5$,
(xx) —CH$_2$CH$_2$OC(O)R$_5$
(xxi) —CH$_2$CH$_2$OC(O)CH(R$_7$)(NHR$_8$),
(xxii) —CH$_2$SH,
(xxiii) —C(O)H,
(xxiv) —CH$_2$CO$_2$R$_9$,
(xxv) —CH$_2$SO$_3$H,
(xxvi) —CH$_2$CH$_2$SO$_3$H,
(xxvii) —CH$_2$CH$_2$PO$_3$H$_2$,
(xxviii) —CH$_2$CH$_2$OCH$_2$PO$_3$H$_2$,
(xxix) —CH$_2$OPO$_3$H$_2$, (xxx) —OCH₂PO₃H₂,
(xxxi) —OH,
(xxxii) —OR₁₀
(xxxiii) —NH₂,
(xxxiv) —NR₁₁R₁₂,
(xxxv) —SH,
(xxxvi) —SR₅,
(xxxvii) —SCN,
(xxxviii) —N₃,
(xxxix) —CN,
(xl) —CONR₁₁R₁₂
(xli) —CH₂CONR₁₁R₁₂
(xlii) —NHOH,
(xliii) —NHOR₅,
(xliv) —NO,
(xlv) —NO₂,
(xlvi) —NHNR₁₁R₁₂
(xlvii) 2-halovinyl,
(xlviii) 3,3,3-trifluoropropenyl,
(xlix) $C_{11}C_{12}$-(alkoxycarbonyl)ethenyl,
(l) 2-carboxyethenyl,
(li) 2-cyanoethenyl,
(lii) difluoromethyl,
(liii) trifluoromethyl,
(liv) 2,2,2-trifluoroethyl,
(lv) 2-haloethyl; and
(lvi) —CH₂N₃;
X is O or S;
Z independently is hydroxy, an ester or amide; and
R₅ is independently H, $C_1$–$C_8$ alkyl or a protecting group.

25. A method for preparation of compounds of formula (V):

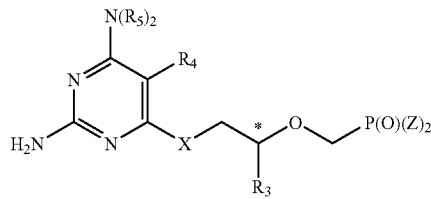

(V)

where
R₃ is methyl, hydroxymethyl, halomethyl or protected hydroxymethyl;
R₄ is selected from:
  (i) $C_1$ to $C_{10}$ alkyl,
  (ii) $C_2$ to $C_{10}$ alkenyl, or,
  (iii) $C_2$ to $C_{10}$ alkynyl,
  (iv) $C_3$–$C_8$ cycloalkyl,
  (v) aryl,
  (vi) heteroaryl,
  (vii) $C_7$–$C_{14}$ arylalkyl,
  (viii) heteroarylalkyl,
  (ix) —CH₂OH,
  (x) —CH₂OR₅
  (xi) —CH₂C(O)R₅,
  (xii) —CH₂R₆,
  (xiii) —CH₂OC(O)R₅
  (xiv) —CH₂OC(O)CH(R₇)(NHR₈),
  (xv) —CH₂NR₉R₁₀,
  (xvi) —CH₂CN,
  (xvii) —CO₂R₅
  (xviii) —CH₂CH₂OH,
  (xix) —CH₂CH₂OR₅
  (xx) —CH₂CH₂OC(O)R₅
  (xxi) —CH₂CH₂OC(O)CH(R₇)(NHR₈),
  (xxii) —CH₂SH,
  (xxiii) —C(O)H,
  (xxiv) —CH₂CO₂R₉,
  (xxv) —CH₂SO₃H,
  (xxvi) —CH₂CH₂SO₃H,
  (xxvii) —CH₂CH₂PO₃H₂,
  (xxviii) —CH₂CH₂OCH₂PO₃H₂,
  (xxix) —CH₂OPO₃H₂,
  (xxx) —OCH₂PO₃H₂,
  (xxxi) —OH,
  (xxxii) —OR₁₀
  (xxxiii) —NH₂,
  (xxxiv) —NR₁₁R₁₂,
  (xxxv) —SH,
  (xxxvi) —SR₅,
  (xxxvii) —SCN,
  (xxxviii) —N₃,
  (xxxix) —CN,
  (xl) —CONR₁₁R₁₂,
  (xli) —CH₂CONR₁₁R₁₂
  (xlii) —NHOH,
  (xliii) —NHOR₅,
  (xliv) —NO,
  (xlv) —NO₂,
  (xlvi) —NHNR₁₁R₁₂
  (xlvii) 2-halovinyl,
  (xlviii) 3,3,3-trifluoropropenyl,
  (xlix) $C_{11}C_{12}$-(alkoxycarbonyl)ethenyl,
  (l) 2-carboxyethenyl,
  (li) 2-cyanoethenyl,
  (lii) difluoromethyl,
  (liii) trifluoromethyl,
  (liv) 2,2,2-trifluoroethyl,
  (lv) 2-haloethyl; and
  (lvi) —CH₂N₃;
R₅ independently is H, $C_1$–$C_8$ alkyl or a protecting group;
X is O or S;
Z independently is hydroxy, an ester or amide; and
* designates a chiral carbon atom;
comprising reacting compound (IVa)

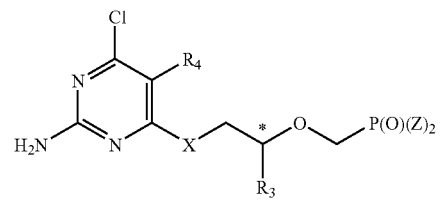

(IVa)

with N(R₅)₂ in anhydrous solvent, alkali hydroxide or alkali carbonate in aqueous solution.

26. A method for preparation of compounds of formula (V):

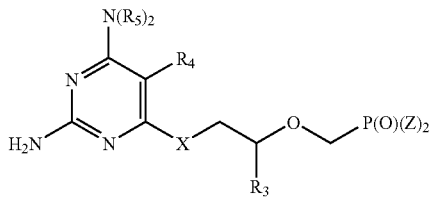

where
R$_3$ is H, methyl, hydroxymethyl, halomethyl or protected hydroxymethyl;
R$_4$ is selected from:
(i) C$_1$ to C$_{10}$ alkyl,
(ii) C$_2$ to C$_{10}$ alkenyl, or,
(iii) C$_2$ to C$_{10}$ alkynyl,
(iv) C$_3$–C$_8$ cycloalkyl,
(v) aryl,
(vi) heteroaryl,
(vii) C$_7$–C$_{14}$ arylalkyl,
(viii) heteroarylalkyl,
(ix) —CH$_2$OH,
(x) —CH$_2$OR$_5$,
(xi) —CH$_2$C(O)R$_5$,
(xii) —CH$_2$R$_6$,
(xiii) —CH$_2$OC(O)R$_5$,
(xiv) —CH$_2$OC(O)CH(R$_7$)(NHR$_8$),
(xv) —CH$_2$NR$_9$R$_{10}$,
(xvi) —CH$_2$CN,
(xvii) —CO$_2$R$_5$,
(xviii) —CH$_2$CH$_2$OH,
(xix) —CH$_2$CH$_2$OR$_5$,
(xx) —CH$_2$CH$_2$OC(O)R$_5$,
(xxi) —CH$_2$CH$_2$OC(O)CH(R$_7$)(NHR$_8$),
(xxii) —CH$_2$SH,
(xxiii) —C(O)H,
(xxiv) —CH$_2$CO$_2$R$_9$,
(xxv) —CH$_2$SO$_3$H,
(xxvi) —CH$_2$CH$_2$SO$_3$H,
(xxvii) —CH$_2$CH$_2$PO$_3$H$_2$,
(xxviii) —CH$_2$CH$_2$OCH$_2$PO$_3$H$_2$,
(xxix) —CH$_2$OPO$_3$H$_2$,
(xxx) —OCH$_2$PO$_3$H$_2$,
(xxxi) —OH,
(xxxii) OR$_{10}$
(xxxiii) —NH$_2$,
(xxxiv) —NR$_{11}$R$_{12}$,
(xxxv) —SH,
(xxxvi) —SR$_5$,
(xxxvii) —SCN,
(xxxviii) —N$_3$,
(xxxix) —CN,
(xl) —CONR$_{11}$R$_{12}$
(xli) —CH$_2$CONR$_{11}$R$_{12}$
(xlii) —NHOH,
(xliii) —NHOR$_5$,
(xliv) —NO,
(xlv) —NO$_2$,
(xlvi) —NHNR$_{11}$R$_{12}$
(xlvii) 2-halovinyl,
(xlviii) 3,3,3-trifluoropropenyl,
(xlix) C$_1$–C$_{10}$ 2-(alkoxycarbonyl)ethenyl, (l) 2-carboxyethenyl,
(li) 2-cyanoethenyl,
(lii) difluoromethyl,
(liii) trifluoromethyl,
(liv) 2,2,2-trifluoroethyl,
(lv) 2-haloethyl; and
(lvi) —CH$_2$N$_3$;
R$_5$ independently is H, C$_1$–C$_8$ alkyl or a protecting group;
X is O or S; and
Z independently is hydroxy, an ester or amide;
comprising reacting compound (IVa)

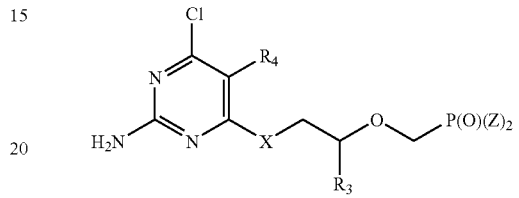

with N(R$_5$)$_2$ in anhydrous solvent, alkali hydroxide or alkali carbonate in aqueous solution.

27. A method of preparation of the compounds of formula (VI)

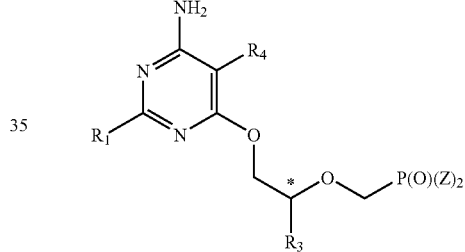

comprising reacting a compound of formula (VII)

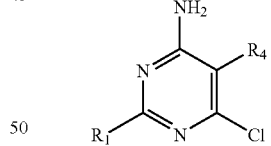

with a compound of the formula (VIII)

in the presence of a base;
where
* designates a chiral carbon atom;
R$_1$ is H, amino or methylsulfanyl;
R$_3$ is methyl, hydroxymethyl, halomethyl or protected hydroxymethyl;
R$_4$ is alkyl, alkenyl, alkynyl, arylalkyl, cycloalkyl, formyl (—CHO), azido (—N$_3$), amino (—NH$_2$), alkylamino (—NR$_2$), hydroxyl (—OH), alkoxy (—OR), cyano (—CN), carboxyl (—COOH), amido (—NRC(O)R, or alkoxycarbonylalkyl; and Z independently is hydroxy, an ester or amide.

28. The method of claim 27 further comprising hydrolyzing Z group to produce a compound of formula (VI) where 1 or 2 Z groups are hydroxy.

29. A method of preparation of the compounds of formula (VI)

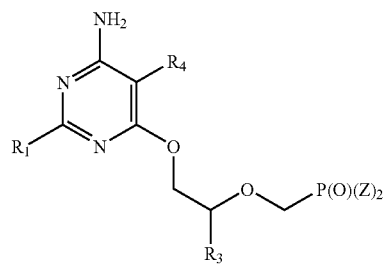
(VI)

comprising reacting a compound of formula (VII)

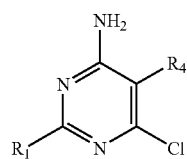
(VII)

with a compound of the formula (VIII)

HOCH$_2$CH$_2$(R$_3$)OCH$_2$P(O)(Z)$_2$   (VIII)

in the presence of a base;
where
R$_1$ is H, amino or methylsulfanyl;
R$_3$ is H, methyl, hydroxymethyl, halomethyl or protected hydroxymethyl;
R$_4$ is alkyl, alkenyl, alkynyl, arylalkyl, cycloalkyl, formyl (—CHO), azido (—N$_3$), amino (—NH$_2$), alkylamino (—NR$_2$), hydroxyl (—OH), alkoxy (—OR), cyano (—CN), carboxyl (—COOH), amido (—NRC(O)R, or alkoxycarbonylalkyl; and
Z independently is hydroxy, an ester or amide.

30. A method of preparation of compounds of formula (XIII)

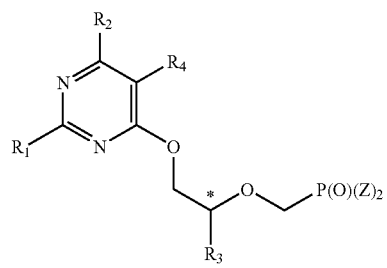
(XIII)

comprising (a) reacting a compound of the formula (IX)

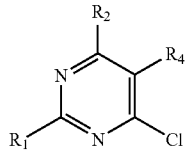
(IX)

with a compound of the formula (X)

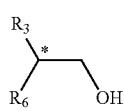
(X)

in the presence of a base without solvent or in the presence of an aprotic solvent, to produce a compound of formula (XI)

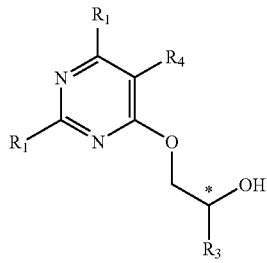
(XI)

and (b) reacting compound (XI) with a compound of the formula (XII)

Y—CH$_2$P(O)(OZ)$_2$   (XII)

in the presence of a base in dimethylformamide or tetrahydrofuran to produce a compound of formula (XIII);
where
* is a chiral carbon atom;
R$_1$ is H, amino or methylsulfanyl;
R$_2$ is H, chloro, hydroxy or amino;
R$_3$ is methyl, hydroxymethyl, halomethyl or protected hydroxymethyl;
R$_4$ is alkyl, alkenyl, alkynyl, arylalkyl, cycloalkyl, formyl (—CHO), azido (—N3), amino (—NH2), alkylamino (—NR$_2$), hydroxyl (—OH), alkoxy (—OR), cyano (—CN), carboxyl (—COOH), amido (—NRC(O)R, or alkoxycarbonylalkyl;
R$_6$ is hydroxy or protected hydroxy; or R$_3$ and R$_6$ are joined by a cyclic acetal or ketal protecting group;
Y is a leaving group; and
Z is hydroxy, amide or an ester.

31. The method of claim 30 further comprising hydrolyzing Z group to produce a compound of formula (XIII) where 1 or 2 Z groups are hydroxyl.

32. A method of preparation of compounds of formula (XIII)

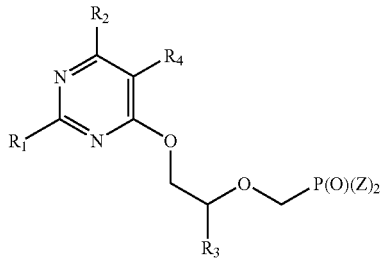

comprising (a) reacting a compound of the formula (IX)

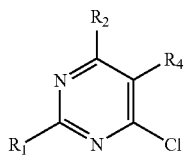

with a compound of the formula (X)

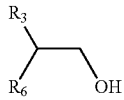

in the presence of a base without solvent or in the presence of an aprotic solvent, to produce a compound of formula (XI)

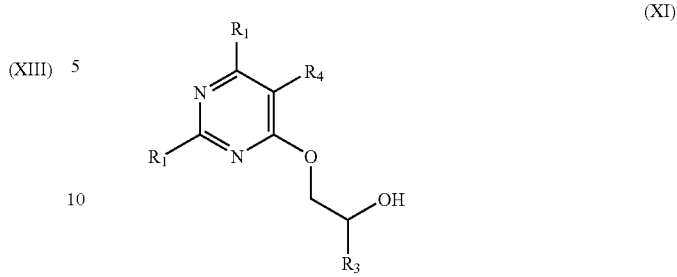

and (b) reacting compound (XI) with a compound of the formula (XII)

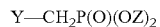

Y—CH$_2$P(O)(OZ)$_2$    (XII)

in the presence of a base in dimethylformamide or tetrahydrofuran to produce a compound of formula (XIII); where $R_1$ is H, amino or methylsulfanyl;

$R_2$ is H, chloro, hydroxy or amino;

$R_3$ is H, methyl, hydroxymethyl, halomethyl or protected hydroxymethyl;

$R_4$ is alkyl, alkenyl, alkynyl, arylalkyl, cycloalkyl, formyl (—CHO), azido (—N3), amino (—NH2), alkylamino (—NR$_2$), hydroxyl (—OH), alkoxy (—OR), cyano (—CN), carboxyl (—COOH), amido (—NRC(O)R, or alkoxycarbonylalkyl;

$R_6$ is hydroxy or protected hydroxy; or $R_3$ and $R_6$ are joined by a cyclic acetal or ketal protecting group;

Y is a leaving group; and

Z is hydroxy, amide or an ester.

33. A method for the treatment of an HIV-1, HIV-2 or hepatitis B viral infection comprising administering a therapeutically effective amount of a compound of claim 1 to a patient in need of such treatment.

34. The method of claim 33 where the virus is HIV-1 or HIV-2.

* * * * *